United States Patent [19]

Tang et al.

[11] Patent Number: 5,726,304
[45] Date of Patent: *Mar. 10, 1998

[54] PORPHOCYANINE AND CNC-EXPANDED PORPHYRINS

[75] Inventors: Hang Tang, Vancouver; Lily Y. Xie, Lethbridge, both of Canada; Tilak Wijesekera, Glen Mills, Pa.; David Dolphin; Ross W. Boyle, both of Vancouver, Canada

[73] Assignee: The University of British Columbia, Vancouver, Canada

[*] Notice: The term of this patent shall not extend beyond the expiration date of Pat. No. 5,407,957.

[21] Appl. No.: 233,632

[22] Filed: Apr. 26, 1994

Related U.S. Application Data

[63] Continuation-in-part of Ser. No. 77,789, Jun. 15, 1993, Pat. No. 5,512,675, which is a continuation-in-part of Ser. No. 968,966, Oct. 30, 1992, Pat. No. 5,405,957.

[51] Int. Cl.$^6$ ............................................. C07D 487/22
[52] U.S. Cl. .......................... 540/145; 540/472; 514/185; 534/14; 534/15
[58] Field of Search ............................. 540/145, 472; 534/14, 15; 514/185

[56] References Cited

PUBLICATIONS

Barnett et al., "Pyrrole chemistry XII. Synthetic Approaches to Cyanopyrroles", *Can J. Chem.*, 58, 409–411 (1979).

Demopolulos et al., "Pyrrole Chemistry. XXVI. A Synthesis of Porphobilinogen from Pyrrole", *Can. J. Chem.*, 61, 2415–76 (1983).

Loader et al., "Pyrrole Chemistry. XXIII. The Cyanation of Substituted Pyrroles with Chlorosulfonyl Isocyanate (CSI). New Syntheses of Pyrrole-3-carbonitriles", *Can. J. Chem.*, 2673–76 (1981).

Dhar et al., "Recent Advances in the Chemistry of Chlorosulfonyl Isocyanate", *Synthesis*, 437–49 (1986).

Floyd et al., "Direct Cyanation of the Furan Nucleus by Chlorosulphonyl Isocyanate", *Tetrahedron*, 39, 3881–85 (1983) and.

Vorbruggen, "Reaktive Isocyanate I. Die Direkte Einfuehrung von Nitril–Gruppen in Ungesattigte System. Eine Einfache Umwandlung von Carbonsauren in Ihre Nitrile", *Tetrahedron Letters*, 13, 1631–34 (1968).

Vonbruggen et al., "The Introduction of Nitrile–Groups into Heterocycles and Conversion of Carboxylic Groups into their Corresponding Nitriles with Chlorosulfonylisocyanate and Triethylamine", *Tetrahedron*, 50:22, 6549–58 (1994).

Primary Examiner—Mukund J. Shah
Assistant Examiner—Pavanaram K. Sripada
Attorney, Agent, or Firm—Morrison & Foerster LLP

[57] ABSTRACT

Compounds of the formula

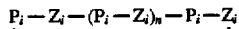

and the metalated forms and salts thereof; wherein n is an integer of 1–4; and wherein each $P_i$ is independently a pyrrole residue of the formula

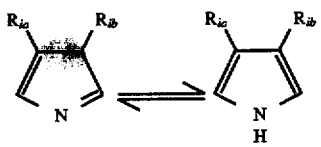

wherein each $R_{ia}$ and $R_{ib}$ is independently a noninterfering substituent, and wherein each $Z_i$ is independently a covalent bond; or is a meso bridging group of the formula

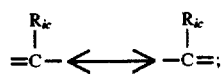

or is an N-meso bridging group of the formula

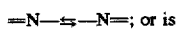

a CC linkage of the formula

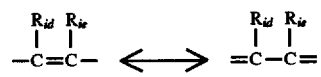

or is a CNCCNC linkage of the formula

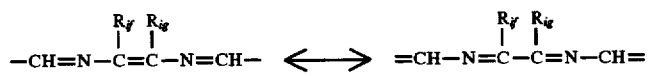

wherein each $R_{ic}$, $R_{id}$, $R_{ie}$, $R_{if}$ and $R_{ig}$ is independently a noninterfering substituent; or is
a CNC linkage of the formula

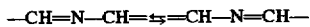

wherein at least one $Z_i$ is said CNC linkage, are disclosed. These compounds are useful in photodynamic therapy and diagnosis. The metalated forms when the metal is paramagnetic are useful as MRI contrast agents.

29 Claims, 3 Drawing Sheets

PORPHOCYANINE AND CNC-EXPANDED PORPHYRINS

RELATED APPLICATIONS

This application is a continuation-in-part of Ser. No. 08/077,789 filed 15 Jun. 1993 now U.S. Pat. No. 5,512,675 which is a continuation-in-part of Ser. No. 07/968,966, filed 30 Oct. 1992 now U.S. Pat. No. 5,405,957, the disclosures of which are incorporated herein by reference.

FIELD OF THE INVENTION

The invention relates to CNC-expanded porphyrins, such as the porphocyanines, to methods for their preparation and the use of these compounds to mediate the detection or destruction of target cells or tissues by light irradiation. In addition, the invention relates to the use of the compounds of the invention in radioimaging and magnetic resonance imaging methods.

BACKGROUND ART

Although considerable effort has been devoted to the synthesis and study of porphyrins and other tetrapyrrolic macrocycles, much less is known about the larger aromatic pyrrole-containing systems, the so-called "expanded porphyrins." Such systems, by virtue of containing a greater number of π electrons, additional coordinating heteroatoms and a larger central binding core, may offer advantages over the porphyrins.

Many of the expanded porphyrin systems contain more than 4 pyrrole rings. The synthesis of saprhyrin from tripyrrane dicarboxylic acid and bipyrroledicarboxaldehyde to yield a pentapyrrole compound was reported several decades ago by Woodward, R. B., Aromaticity Conference, Scheffield, England, 1966. See also, Broadhurst et al., *J Chem Soc Perkins Trans* (1972) 1:2111 and Bauer et al. *J Am Chem Soc* (1983) 105:6429). The synthesis of smaragdyrin from bipyrroledicarboxaidehyde and pyrroledipyrromethane dicarboxylic acid was reported in 1970 by M. M. King. (Ph.D. Dissertation, Harvard University, Cambridge, Ma.)

The uranyl complex of superphthalocyanine is another pentapyrrolic macrocyclic compound of historical importance. This compound was prepared by direct template condensation of dicyanobenzene with uranyl dichloride, however, the free base is unstable (Day et al. *J Am Chem Soc* (1975) 97:4519). Demetalation resulted in contraction of the ring to form phthalocyanine (Marks, T. J. and D. R. Stojakovic *J Am Chem Soc* (1978) 100:1695).

Gossauer synthesized the first hexaphyrin by condensing a bis-α-tripyrrane with a tripyrrane dialdehyde, followed by oxidation (*Bull Soc Chim Belg* (1983) 92:793). Of the six methene bridges present in the hexaphyrin, two have E configuration (Id.). Charriere reported that hexaphyrin forms bimetallic complexes with several transition metals (1987, Thesis, University de Fribourg, Suisse). Another hexapyrrolic system, rubyrin, has been recently synthesized and structurally characterized (Sessler et al. *Angew Chem int Ed Engl* (1991a) 30:977).

Vinylogous porphyrins or platyrins are another important class of pyrrole-containing macrocycles first described by R. A. Berger and E. LeGoff (*Tetra Lett* (1978) 44:4225; see also, LeGoff, E. and O. G. Weaver *J Org Chem* (1977) 52:711; and Franck et al. *Proc SPIE int Soc Opt Eng*, Ser 5 (1988) 997:107). These compounds are generally synthesized by reacting a dipyrromethane with an acrylaldehyde-substituted dipyrromethane (Beckman et al. *Angew Chem int Ed Engl* (1990) 29:1395). Bisvinylogous expanded porphyrins were further expanded to tetravinylogous porphyrins in which all four of the meso bridges are enlarged. Tetravinylogous porphyrins are made by an acid-catalyzed self-condensation of the N-protected, pyrrole-substituted allyl alcohol. Tetravinylogous porphyrins have a very intense Soret-like band shift of more than 150 nm from that of the normal porphyrins (Gosmann, M. and B. Franck *Angew Chem Int Ed Engl* (1986) 25:1100; Knübel, G. and B. Franck *Angew Chem int Ed Engl* (1988) 27:1170). In addition, the synthesis of bisvinylogous porphycene has recently been reported (Jux et al. *Angew Chem int Ed Engl* (1990) 29:1385; Vogel et al. *Angew Chem int Ed Engl* (1990) 29:1387).

Schiff-base compounds represented by the texaphyrins comprise another class of pyrrole containing macrocycles (Sessler et al. *J Org Chem* (1987) 52:4394; Sessler et al. *J Am Chem Soc* (1988) 110:5586); Sessler, J. L. et al. *Acc Chem Res* (1994) 27:43–50. Texaphyrins are synthesized by acid-catalyzed condensation of tripyrrane dialdehyde with o-phenylenediamine. Several texaphyrins have been prepared using similar strategies (Sessler et al. (1991) Abstract of the 201st Natl Soc Mtg, Inorganic Division; Sessler et al. *Inorg Chem* (1992) 28:529).

The use of porphyrins, combined with irradiation, for the detection and treatment of malignant cells has, by this time, some considerable history. (See, e.g., *Porphyrin Photosensitization* (Kessel, D. et al., eds. Plenum Press, 1983). Certain porphyrins seem "naturally" capable of localizing malignant cells. When irradiated, porphyrins have two properties which make them useful. First, when irradiated with ultraviolet or visible light, they may fluoresce, and thus be useful in diagnostic methods related to detection of malignancy (see, for example, Kessel et al., supra; Gregory, H. B. Jr. et al., *Ann Surg* (1968) 167:827–829).

In addition, when irradiated with light, certain porphyrins exhibit a cytotoxic effect on the cells in which they are localized (see, for example, Diamond, I. et al., Lancet (1972) 2:1175–1177; Dougherty, T. J. et al., Cancer Research (1978) 38:2628–2635; Dougherty, T. J. et al., *The Science of Photo Medicine* 625–638 (J. D. Regan & J. A. Parrish, eds., 1982); Dougherty, T. J. et al., *Cancer: Principles and Practice of Oncology* 1836–1844 (V. T. DeVita Jr. et al., eds., 1982). Certain of the expanded porphyrins such as sapphyrin, texaphyrin and vinylogous porphyrins possess unique long-wavelength and singlet oxygen producing properties which also make them attractive as potential photosensitizers for use in tumor phototherapy (Maiya et al. *J Phys Chem* (1990) 94:3597; Sessler et al. *SPIE Soc* (1991) 1426:318; Franck et al., supra).

Porphyrins, such as hematoporphyrin, monohydrobenzoporphyrin derivatives (BPDs) and porfimer sodium have been conjugated to immunoglobulins specific for targeted cells to refine their ability to home to the desired cells or tissue.

One problem ancillary to the practice of photodynamic therapy is that the wavelength for irradiation required to activate certain porphyrins is in the range of 630 nm, which wavelength is also readily absorbed by other porphyrins and natural chromophores normally present in the blood and other tissues. Therefore, the depth of the effective treatment has been limited to a few millimeters because of blocking effects of light-absorbing natural chromophores such as hemoglobin. When greater penetration is desired it is desirable to administer compounds to mediate the effects of irradiation which can be excited at longer wavelengths such as the BPDs thus avoiding the blocking effects of natural chromophores present throughout the subject organism.

In addition to phototherapy, expanded porphyrins are useful in magnetic resonance imaging (MRI). MRI is a noninvasive, nonionizing method that allows normal and abnormal tissue to be observed and recognized at the early stages of development. At this time MRI has a significant drawback, in that the degree of signal enhancement for diseased versus normal tissues is often insufficient to allow this method to be used in many clinical situations. To overcome this problem, contrast reagents for MRI have been developed. Paramagnetic metal complexes, such as those derived from gadolinium(III) (Gd) have recently proven particularly efficient in clinical trials.

To date, the coordination of gadolinium in MRI contrast agents has been achieved using carboxylate-type ligands including porphyrins, but more successfully with texaphrins. (See, for example, Lauffer, R. B. *Chem Rev* (1987) 87:901; Kornguth et al. *J Neurosurg* (1987) 66:898; Koenig et al. *Invest Radiol* (1986) 21:697; Chacheris et al. *Inorg Chem* (1987) 26:958; Loncin et al. *Inorg Chem* (1986) 25:2646; Chang, C. A. and V. C. Sekhar *Inorg Chem* (1987) 26:1981). Sessler et al. reported that texaphyrin forms an extremely stable Gd(III) complex in vitro (Sessler et al. *Inorg Chem* (1989) 28:3390). Gd(III) does not form stable complexes with normal porphyrins. In addition to Gd(III), texaphyrin has been reported to form complexes with a variety of transition metals such as Cd and Eu (Sessler, J. L. and A. K. Burrell *Top Cur Chem* (1992) 161:177).

DISCLOSURE OF THE INVENTION

The invention provides novel light-absorbing compounds suitable for use in detecting and/or treating target tissues, cells and pathogens. The compounds of the invention can be utilized in photodynamic therapy and in diagnosis in a manner analogous to that in which the porphyrins, phthalocyanines, BPDs, and related compounds can be used. If desired, the invention compounds may be administered in relatively low dosage due to their ability to absorb radiation in an energy range outside of that normally absorbed by the components present in high concentration in blood or other tissues, in particular the porphyrin residues normally associated with hemoglobin and myoglobin. This is advantageous when penetration of tissues by light is required. In some instances, where superficial treatment is sufficient, shorter wavelengths can be used.

These compounds are preferentially retained in target tissues and cells as compared to nontarget tissues and cells, though this property may not be necessary for effective treatment. See, e.g., U.S. Ser. No. 07/948,113 filed 21 Sep. 1992 and 07/979,546 filed 20 Nov. 1992, the contents of which are incorporated herein by reference.

Thus, in one aspect, the invention is directed to CNC-expanded porphyrins of the formula $$P_i—Z_i—(P_i—Z_i)_n—P_i—Z_i \quad (1)$$

wherein n=1–4;
wherein each $P_i$ is independently a pyrrole residue of the formula

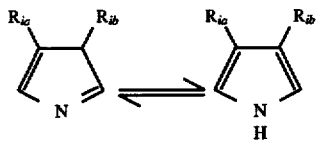

wherein each $R_{ia}$ and $R_{ib}$ is independently a noninterfering substituent, and wherein each $Z_i$ is independently a covalent bond; or is a meso bridging group of the formula

an N-meso bridging group of the formula

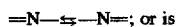

a CC linkage of the formula

or is a CNCCNC linkage of the formula

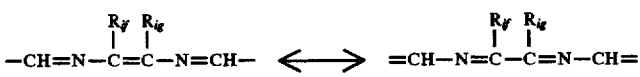

wherein each $R_{ic}$, $R_{id}$, $R_{ie}$, $R_{if}$ and $R_{ig}$ is independently a noninterfering substituent; or is
a CNC linkage of the formula

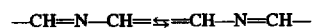

wherein at least one $Z_i$ is said CNC linkage.

In the compounds of the invention at least one $Z_i$ is said CNC linkage. The compounds of the invention also include the metalated forms and the salts of the compound of formula (1).

The prototype of this group of "CNC-expanded porphyrins" is porphocyanine, as described below.

In other aspects, the invention is directed to pharmaceutical and diagnostic compositions containing the compounds of the invention, to conjugates wherein the invention compounds are covalently linked with specific targeting agents, such as immunoglobulins, and to the use of these compounds or conjugates in photodynamic therapy and diagnosis. In another aspect, the invention is directed to forms of the invention compounds suitable for use as radioimaging and magnetic resonance imaging contrast agents, as well as methods of using these. Another aspect relates to synthesis of the invention compounds.

MODES OF CARRYING OUT THE INVENTION

The compounds of the invention, designated herein "CNC-expanded porphyrins", contain at least 3 pyrrole nuclei linked through covalent bonds, or through optionally substituted conventional meso linkages found natively in porphyrins, or through N-meso linkages found in phthalscyanines, or through optionally substituted CC linkages as found in the phorphacenes or through optionally substituted CNCCNC linkages analogous to the o-phenylene diamine linkages found in the texaphins, or by CNC linkages, but wherein at least one linkage is a CNC linkage of the formula

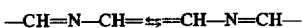

The members of one specific class belonging to this group are designated porphocyanines. These are represented by the formula

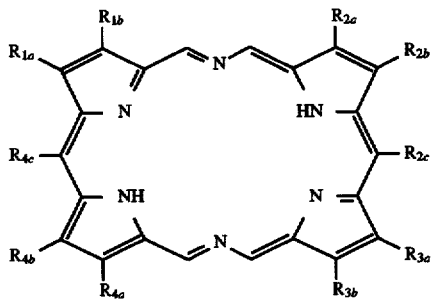

The various R substituents are those which do not interfere with the basic porphocyanine nucleus in its ability to absorb light of appropriate wavelengths and to achieve at least one desired effect, such as mediating the destruction of target tissues and cells in a photodynamic therapy context, serving as an MRI contrast agent, and the like. The nature of suitable R substituents which will not interfere is further discussed below. However, it can be stated that a wide variety of subemployed may be employed without interfering with the usefulness of these compounds. The appropriate choice of these noninterfering substituents will depend on the specific intended use. For example, if intended for in vivo use, the substituents must be nontoxic. When employed in vitro, especially if the possibility for removal of the compounds of the invention from the appropriately treated material is available, this may not be of concern. Those or ordinary skill will understand the parameters that constrain the choice of each $R_i$.

In addition to the compounds of formula (1a), other CNC-expanded porphyrins are included in the scope of the invention. In one preferred embodiment, where n=2, formula (1) can be represented by

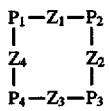

wherein each $P_i$ and $Z_i$ is as above defined, illustrative of these —CNC— compounds where n=2 are the compounds of formulas (1b)–(1e):

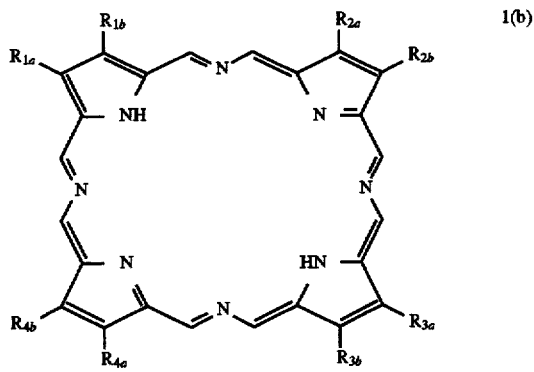

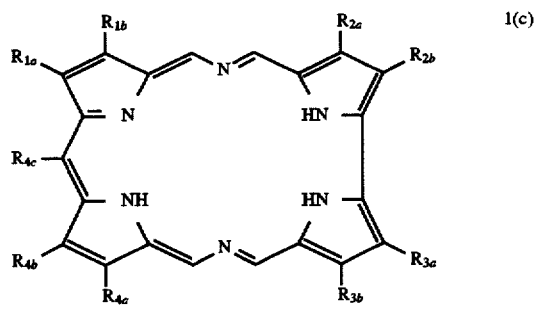

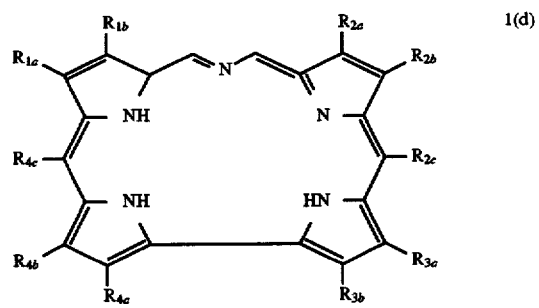

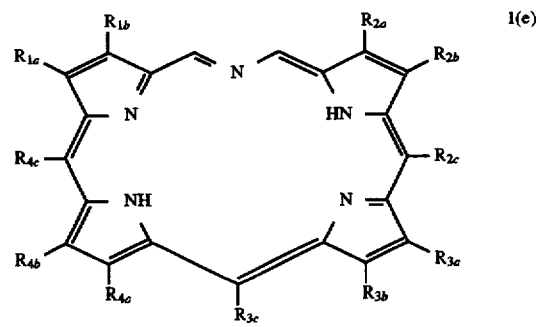

or, generically,

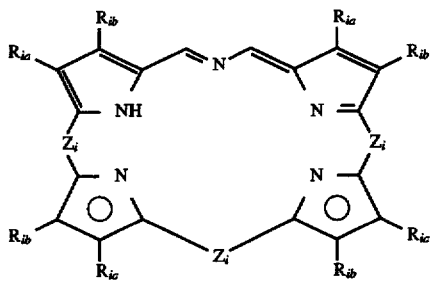

1(f)

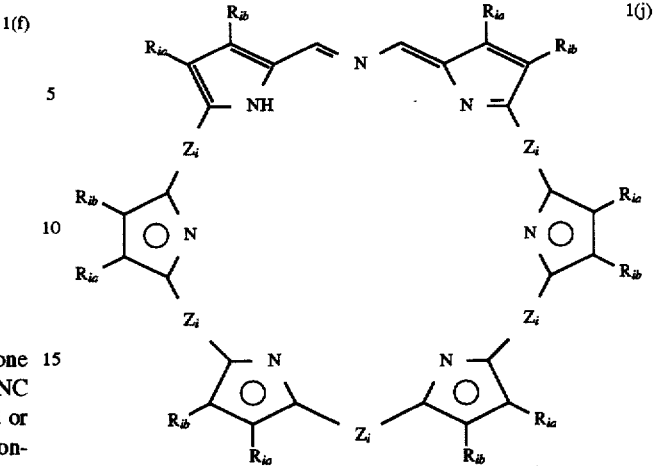

1(j)

As seen from these illustrative formulas, at least one bridge between the four pyrrole nuclei must be a CNC linkage. Otherwise, the linkage may be a covalent bond or the conventional meso single-atom methine linkage optionally substituted by $R_{ic}$, or the other linkages described above. The resultant arrangement of π-bonds in the CNC porphyrins of the invention will be dependent on the choice of linkage, as is understood by those of ordinary skill in organic chemistry. For example, replacing an odd number of meso linkages with CNC can convert an aromatic system to a nonaromatic, albeit stable one; replacement of an even number retains aromaticity.

Additional embodiments include those wherein n=1:

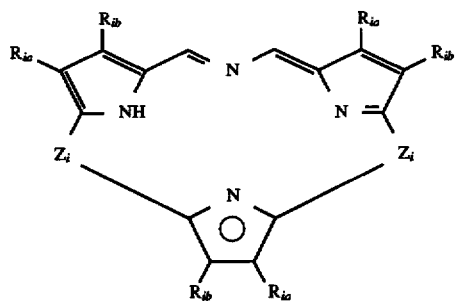

1(g)

or wherein n = 3:

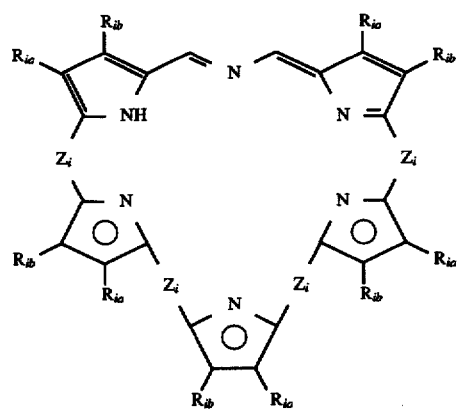

Figure 1:
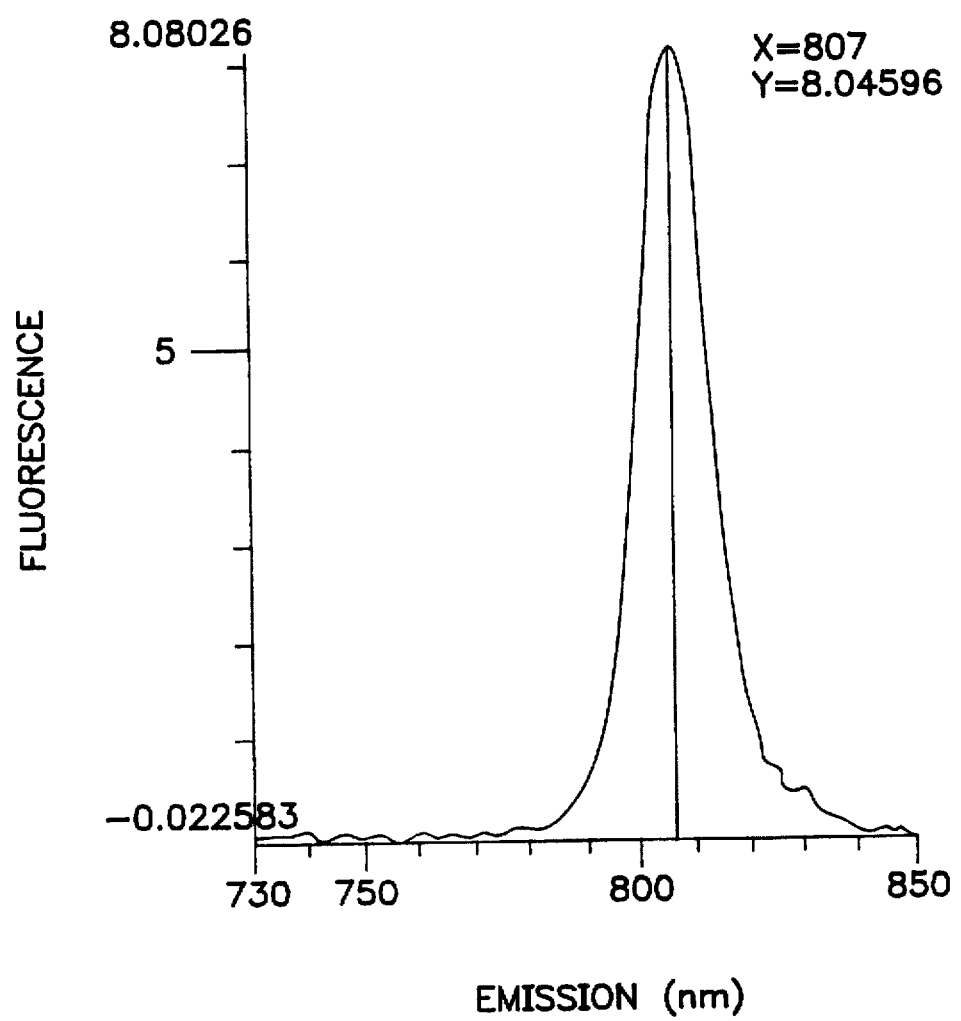
FIG. 1 shows the flusorescence emission spectrum of octaethylporphocyanine in the free-base form.
Figure 2:
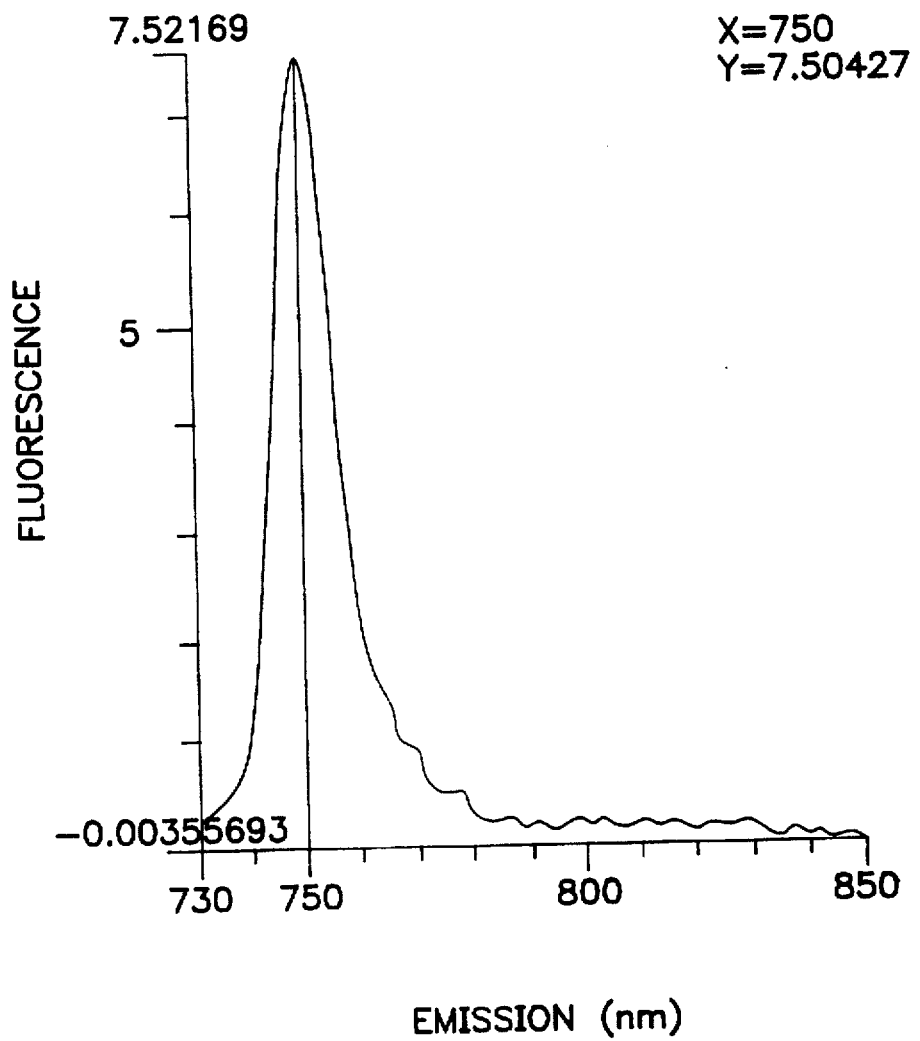
FIG. 2 shows the flusorescence emission spectrum of octaethylporphocyanine in the acid-addition-salt form.
Figure 3:
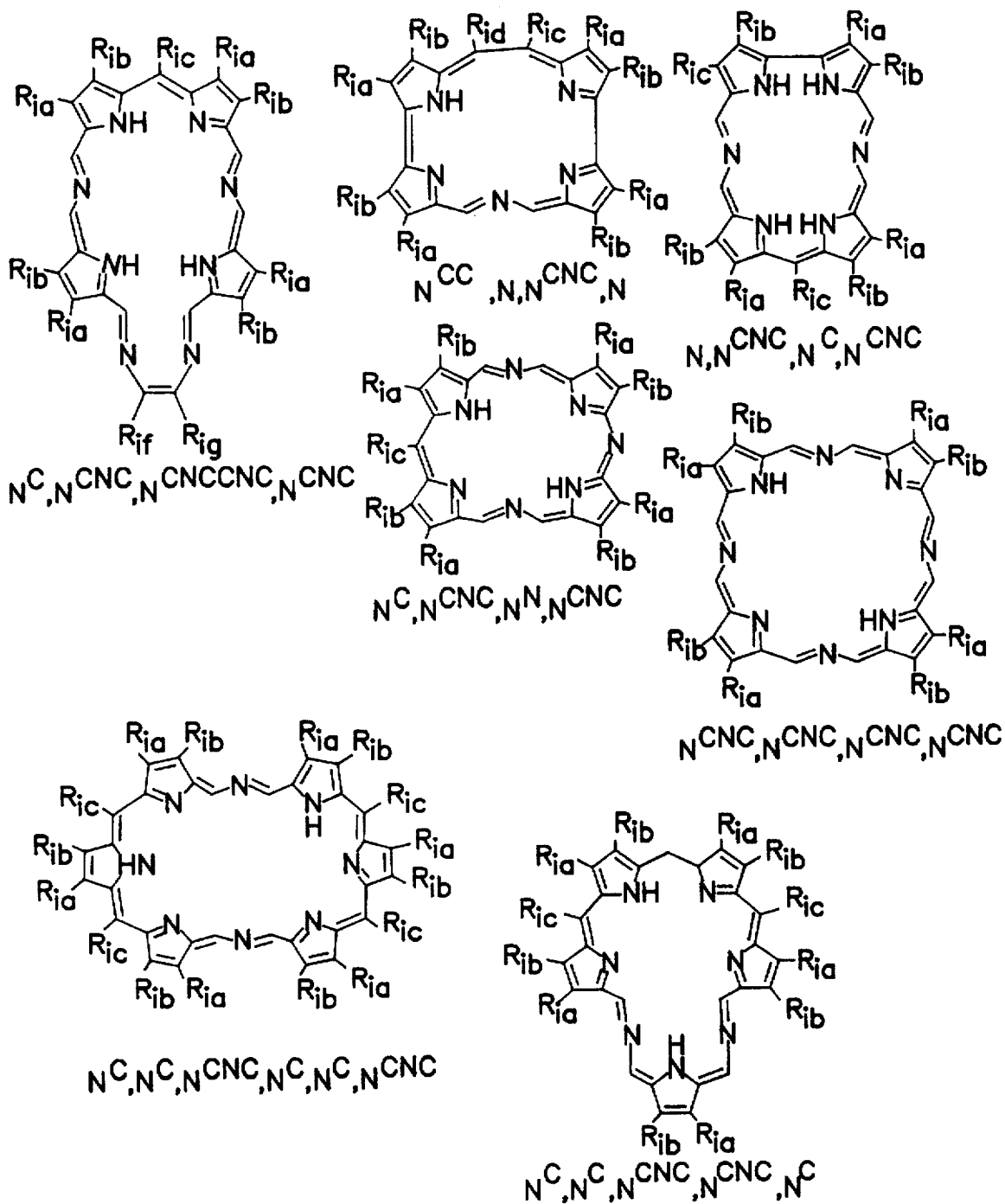
FIG. 3 shows some preferred embodiments of the invention compounds.

1(h)

or wherein n = 4:

Particularly preferred are those embodiments shown in FIG. 3.

With respect to the substituents $R_{ia}$, $R_{ib}$ and $R_{ic}$, $R_{id}$, $R_{ie}$, $R_{if}$ and $R_{ig}$ in general, each $R_i$ is independently H, halo, nitro, cyano, —NR'$_2$, —SR', —OR', —SOR', —SO$_2$R', —COOR', —CONR'$_2$, optionally substituted alkyl, optionally substituted alkenyl, optionally substituted alkynyl, optionally substituted aryl, or optionally substituted arylalkyl. The substituent R' denotes hydrogen or alkyl (1–6C). Amino, sulfhydryl and hydroxyl substituents may also be acylated (1–6C). Suitable substituents for said optional substitutions include those named above, i.e., halo, nitro, cyano, —NR'$_2$, —SR', —OR', and the like. Of course, aromatic nuclei may also be substituted by alkyl, alkenyl or alkynyl groups.

As used herein, alkyl, alkenyl and alkynyl are defined conventionally as hydrocarbyl substituents containing 1–6C, are either saturated or unsaturated, and are straight-chain, branched or cyclic moieties. Thus, alkyl would include methyl, tertiary butyl, cyclohexyl, n-hexyl and the like; alkenyl would include these carbon backbones with one or more double bonds; and alkynyl would include similar carbon frameworks with one or more triple bonds. Arylalkyl (5–18C) refers to an aryl substituent linked to the CNC-expanded porphyrin nucleus through an alkylene group, where alkylene is defined in a manner corresponding to the definition of alkyl (1–6C).

By "aryl" is meant an aromatic moiety of 4–12C, optionally containing one or more heteroatoms. Thus, suitable aryl groups include phenyl, naphthyl, pyridyl, pyrimidyl, quinolyl, and the like.

Where the substituents contain carboxylic acid or amino substitutions, the relevant salts are also included within the scope of the invention compounds.

Salts of —COOH can be derived from inorganic or organic bases, including pharmaceutically acceptable nontoxic inorganic and organic bases. Suitable inorganic bases include sodium, potassium, lithium, ammonium, calcium, and magnesium, hydroxides, and the like. Particularly preferred are the potassium and sodium salts. Pharmaceutically acceptable organic nontoxic bases include primary, secondary, tertiary and quaternary amines including cyclic amines, and basic ion-exchange resins. Examples include isopropylamine, trimethylamine, ethanolamine, dicyclohexylamine, lysine, arginine, histidine, caffeine, procaine, choline, betaine, glucosamine, theobromine, purines, piperazine, polyamine resins, and the like.

Any amino groups contained in the substituents may also be present in the form of their acid-addition salts. In addition, the CNC-expanded porphyrin nucleus itself may be present in the form of an acid-addition salt. These salts are formed from inorganic acids such as hydrochloric, sulfuric and phosphoric acid or with organic acids such as acetic, oxalic, benzoic acid and the like.

Conversion of the invention compounds from free acid or free base to the corresponding salt forms and vice versa are conducted by methods well understood in the art.

Preferred embodiments of $R_{ia}$ and $R_{ib}$ include hydrogen, optionally substituted alkyl, optionally substituted aryl and optionally substituted arylalkyl. A particularly preferred substituent is carboxyl. Most preferred are hydrogen and alkyl. In addition, while each $R_{ia}$ and $R_{ib}$ is independently determined, symmetries in the choice of these substituents facilitate the preparation of the compounds since the number of components in the resulting product mixture is reduced. While chromatographic separation techniques are adequate to permit an arbitrary number of components to be separated from the product mixture, yields are increased when the number of possible products is reduced. Thus, particularly preferred are compounds of the invention wherein all $R_{ia}$ are the same and all $R_{ib}$ are the same, especially where all $R_{ia}$ and $R_{ib}$ are the same. Another preferred embodiment is that wherein in the compound of formula 1(a), $R_{1a}$, $R_{1b}$, $R_{4a}$ and $R_{4b}$ are the same and wherein $R_{2a}$, $R_{2b}$, $R_{3a}$ and $R_{3b}$ are the same as each other although different from $R_{1a}$, $R_{1b}$, $R_{4a}$, and $R_{4b}$.

Particularly preferred embodiments of $R_{ic}$–$R_{ig}$ include H and optionally substituted aromatic (aryl) substituents. Particularly preferred embodiments of $R_{ic}$ are H and optionally substituted phenyl.

Illustrative preferred embodiments of the invention compounds wherein n=1 are:

1. $Z_1$ is CNC, $Z_2$ is meso wherein $R_{2c}$ is H, $Z_3$ is a covalent bond, $R_{1a}$ and $R_{2b}$ are H, and $R_{1b}$, $R_{2a}$, $R_{3a}$ and $R_{3b}$ are methyl;
2. $Z_1$ is CNC, $Z_2$ is meso wherein $R_{2c}$ is phenyl, $Z_3$ is a covalent bond, $R_{1a}$, $R_{2a}$, $R_{3a}$ and $R_{3b}$ are $(CH_2)_2COOH$, $R_{1b}$ is methyl and $R_{2b}$ is H;
3. $Z_1$ is CNC, $Z_2$ is CNCCNC wherein $R_{2f}$ and $R_{2g}$ are H, $Z_3$ is CC wherein $R_{3d}$ and $R_{3e}$ are H, and wherein $R_{1a}$ and $R_{2b}$ are H, and $R_{1b}$, $R_{2a}$, $R_{3a}$ and $R_{3b}$ are methyl;
4. $Z_1$ is CNC, $Z_2$ is CNCCNC wherein $R_{2f}$ and $R_{2g}$ are phenyl, $Z_3$ is CC wherein $R_{3d}$ and $R_{3e}$ are phenyl, $R_{2a}$, $R_{3a}$ and $R_{3b}$ are $(CH_2)_2COOH$, $R_{1b}$ is methyl and $R_{2b}$ is H,
5. $Z_1$ is CNC, $Z_2$ is CNCCNC wherein $R_{2f}$ is phenyl and $R_{2g}$ is H, and $Z_3$ a CC linkage wherein $R_{3d}$ is phenyl and $R_{3e}$ is H and wherein $R_{1a}$, $R_{2a}$ and $R_{3a}$ are phenyl and $R_{1b}$, $R_{2b}$ and $R_{3b}$ are H.

Preferred embodiments wherein n=2 are:

1. $Z_1$ is CNC, $Z_2$ is N-meso, $Z_3$ is meso wherein $R_{3c}$ is methyl, and $Z_4$ is CNC and wherein $R_{1a}$ and $R_{2b}$ are H and $R_{1b}$, $R_{2a}$, $R_{3a}$, $R_{3b}$, $R_{4a}$ and $R_{4b}$ are methyl;
2. $Z_1$ is CNC, $Z_2$ is N-meso, $Z_3$ is meso wherein $R_{3c}$ is phenyl and $Z_4$ is CNC and wherein $R_{1a}$, $R_{2a}$, $R_{3a}$, $R_{3b}$ and $R_{4a}$ are $(CH_2)_2COOH$ and $R_{1b}$, $R_{2b}$ and $R_{4b}$ are H;
3. $Z_1$ is CNC, $Z_2$ is N-meso, $Z_3$ is meso wherein $R_{3c}$ is H, and $Z_4$ is CNC and wherein $R_{1a}$, $R_{2a}$, $R_{3a}$ and $R_{4a}$ are phenyl and $R_{1b}$, $R_{2b}$, $R_{3b}$ and $R_{4b}$ are ethyl;
4. $Z_1$ is CNC, $Z_2$ is CNCCNC wherein $R_{2f}$ and $R_{2g}$ are both phenyl, $Z_3$ is a CC linkage wherein $R_{3d}$ and $R_{3e}$ are H, and $Z_4$ is a covalent bond and wherein $R_{1a}$ and $R_{2b}$ are H and $R_{1b}$, $R_{2a}$, $R_{3a}$, $R_{3b}$, $R_{4a}$ and $R_{4b}$ are methyl;
5. $Z_1$ is CNC, $Z_2$ is CNCCNC wherein $R_{2f}$ and $R_{2g}$ are H, or $Z_3$ is a CC linkage wherein $R_{3d}$ is ethyl and $R_{3e}$ is H, and $Z_4$ is meso wherein $R_{4c}$ is ethyl and wherein $R_{1a}$, $R_{2a}$, $R_{3a}$, $R_{3b}$ and $R_{4a}$ are $(CH_2)_2COOH$ and $R_{1b}$, $R_{2b}$ and $R_{4b}$ are H;
6. $Z_1$ is CNC, $Z_2$ is CNCCNC wherein $R_{2f}$ is ethyl and $R_{2g}$ is H, $Z_3$ is meso wherein $R_{3c}$ is phenyl and $Z_4$ is a CC linkage wherein $R_{3d}$ and $R_{3e}$ are methyl and wherein $R_{1a}$, $R_{2a}$, $R_{3a}$ and $R_{4a}$ are phenyl and $R_{1b}$, $R_{2b}$, $R_{3b}$ and $R_{4b}$ are ethyl.

In instances where n=3, preferred compounds are:

1. $Z_1$ is CNC, $Z_2$ is meso wherein $R_{2c}$ is methyl, $Z_3$ is meso wherein $R_{3c}$ is methyl, $Z_4$ is a covalent bond and $Z_5$ is CNC and wherein $R_{1a}$, $R_{2a}$, $R_{3a}$, $R_{4a}$ and $R_{5a}$ are methyl and $R_{1b}$, $R_{2b}$, $R_{3b}$, $R_{4b}$ and $R_{5b}$ are H;
2. $Z_1$ is CNC, $Z_2$ is N-meso, $Z_3$ is meso wherein $R_{3c}$ is phenyl, $Z_4$ is CNC and $Z_5$ is CC wherein $R_{5d}$ and $R_{5e}$ are phenyl, and wherein $R_{1a}$, $R_{1b}$, $R_{3a}$, $R_{3b}$, $R_{5a}$ and $R_{5b}$ are $(CH_2)_2COOH$ and $R_{2a}$, $R_{2b}$, $R_{4a}$ and $R_{4b}$ are methyl;
3. $Z_1$ is CNC, $Z_2$ is N-meso, $Z_3$ is meso wherein $R_{3c}$ is H, $Z_4$ is N-meso, and $Z_5$ is CNC and wherein $R_{1a}$, $R_{3a}$ and $R_{5a}$ are phenyl, $R_{1b}$, $R_{3b}$ and $R_{5b}$, are H and $R_{2a}$, $R_{2b}$, $R_{4a}$ and $R_{4b}$ are methyl;
4. $Z_1$ is CNC, $Z_2$ is meso wherein $R_{2c}$ is methyl, $Z_3$ is CNCCNC wherein $R_{3f}$ and $R_{3g}$ are phenyl, $Z_4$ is N-meso, $Z_5$ is a CC linkage wherein $R_{3d}$ and $R_{3e}$ are H, and wherein $R_{1a}$ and $R_{2b}$ are H and $R_{1b}$, $R_{2a}$, $R_{3a}$, $R_{3b}$, $R_{4a}$ and $R_{4b}$ are ethyl;
5. $Z_1$ is CNC, $Z_2$ is CNCCNC wherein $R_{2f}$ and $R_{2g}$ are H, $Z_3$ is a CC linkage wherein $R_{3d}$ is ethyl and $R_{3e}$ is H, $Z_4$ is meso wherein $R_4c$ is ethyl and $Z_5$ is a covalent bond, and wherein $R_{1a}$, $R_{2a}$, $R_{3a}$, $R_{3b}$ and $R_{4a}$ are $(CH_2)_2COOH$ and $R_{1b}$, $R_{2b}$, $R_{4b}$, $R_{5a}$ and $R_{5b}$ are H;
6. $Z_1$ is CNC, $Z_2$ is CNCCNC wherein $R_{2f}$ is ethyl and $R_{2g}$ is H, $Z_3$ is meso wherein $R_{3c}$ is phenyl, $Z_4$ is a CC linkage wherein $R_{4d}$ and $R_{4e}$ are methyl and $Z_5$ is CNC, and wherein $R_{1a}$, $R_{2a}$, $R_{3a}$, $R_{4a}$ and $R_{5a}$ are methyl and $R_{1b}$, $R_{2b}$, $R_{3b}$, $R_{4b}$ and $R_{5b}$ are ethyl;
7. $Z_1$ is CNC, $Z_2$ is a CC linkage wherein $R_{2d}$ and $R_{2e}$ are phenyl, $Z_3$ is CNCCNC wherein $R_{3f}$ and $R_{3g}$ are H, $Z_4$ is N-meso and $Z_5$ is meso wherein $R_{5c}$ is methyl and wherein $R_{1a}$, $R_{1b}$, $R_{3a}$, $R_{3b}$, $R_{5a}$ and $R_{5b}$ are $(CH_2)_2COOH$ and $R_{2a}$, $R_{2b}$, $R_{4a}$ and $R_{4b}$ are methyl;
8. $Z_1$ is CNC, $Z_2$ is a covalent bond, $Z_3$ is meso wherein $R_{3c}$ is phenyl, $Z_4$ is CNC and $Z_5$ is a CC linkage wherein $R_{5d}$ and $R_{5e}$ are methyl and wherein $R_{1a}$, $R_{3a}$ and $R_{5a}$ are phenyl, $R_{1b}$, $R_{3b}$ and $R_{5b}$ are H and $R_{2a}$, $R_{2b}$, $R_{4a}$ and $R_{4b}$ are methyl.

For compounds wherein n=4, preferred embodiments include:

1. $Z_1$ and $Z_6$ are CNC, $Z_2$ and $Z_5$ are CC linkages where all of $R_{2d}$, $R_{2e}$, $R_{5d}$ and $R_{5e}$ are phenyl, and $Z_3$ and $Z_4$ are meso where $R_{3c}$ and $R_{4c}$ are ethyl, and wherein $R_{1a}$, $R_{2a}$, $R_{3a}$, $R_{4a}$, $R_{5a}$ and $R_{6a}$ are i-propyl and $R_{1b}$, $R_{2b}$, $R_{3b}$, $R_{4b}$, $R_{5b}$ and $R_{6b}$ are $(CH_2)_2COOH$;
2. $Z_1$ is CNC, $Z_2$ and $Z_4$ are N-meso, $Z_3$ and $Z_5$ are covalent bonds and $Z_6$ is meso wherein $R_{6c}$ is H and $R_{1a}$, $R_{2a}$, $R_{3a}$, $R_{4a}$, $R_{5a}$ and $R_{6a}$ are phenyl and $R_{1b}$, $R_{2b}$, $R_{3b}$, $R_{4b}$, $R_{5b}$ and $R_{6b}$ are methyl.

The possibility of obtaining CNC-expanded porphyrins with a multiplicity of substituents has the advantage that the properties of the core CNC-expanded porphyrin nucleus can be modified by the choice of such substituents. For example, solubility of the compounds can be enhanced by employing substituents with polar groups. By altering the symmetry of the arrangement of these groups, the compounds can be made ampiphilic, i.e., the compound will have a patterned distribution of + and − charges. This property is helpful in solving problems of biodistribution—membrane transition and the like. In addition, the light-absorbing qualities of the core nucleus can be modified to some extent by conjugated π-bonds in the substituents giving the usual auxochromic shift.

Metalation/Addition of Radio Isotopes

The CNC-expanded porphyrin compounds of the present invention include those where the CNC-expanded porphyrin itself is coupled with a radioisotope for radioimaging (scintigraphic imaging) or with certain metals for use as ions a magnetic resonance image contrast agent, or simply as a convenient form of the compound. Examples of radioisotopes which would be useful labels include Iodine-123, iodine-131, Technetium-99m, Indium-111 and gallium-67. Examples of metals which would be appropriate as MRI contrast agents include paramagnetic ions of elements such as Gd, Fin, Eu, Dy, Pr, Pa, Cr, Co, Fe, Cu, Ni, Ti, and V, preferably Gd and Fin.

Conjugates of the Invention Compounds

For use in some contexts, it is helpful to link the compounds of the invention to a target-specific moiety such as an immunoglobulin or a ligand for a receptor. The ability of the invention compounds to home to diseased tissues and cells such as tumors, if desired, can be enhanced by coupling the compound to a moiety that specifically binds epitopes or receptors located on the surface of such target tissues or cells.

Thus, target-specific moieties within the present invention include ligands such as steroids, such as estrogen and testosterone and derivatives thereof, peptides comprising ligands for T cell receptors, saccharides, such as mannose for which monocytes and macrophages have receptors, and H2 agonists.

Target-specific moieties may also be immunospecific components. The TSM may be derived from polyclonal or monoclonal antibody preparations and may contain whole antibodies or immunologically reactive fragments of these antibodies such as (F(ab')$_2$, Fab, or Fab' fragments. Use of such immunologically reactive fragments as substitutes for whole antibodies is well known in the art. See, for example, Spiegelberg, H. L., Immunoassays in the Clinical Laboratory (1978) 3:1–23.

Polyclonal antisera are prepared in conventional ways by injecting a suitable mammal with antigen to which antibody is desired, assaying the antibody level in serum against the antigen, and preparing antisera when the titers are high. Monoclonal antibody preparations may also be prepared conventionally such as by the method of Koehler and Milstein using peripheral blood lymphocytes or spleen cells from immunized animals and immortalizing these cells either by viral infection, by fusion with myelomas, or by other conventional procedures, and screening for production of the desired antibodies by isolated colonies. Formation of the fragments from either monoclonal or polyclonal preparations is effected by conventional means as described by Spiegelberg, H. L., supra.

Particularly useful antibodies exemplified herein include the monoclonal antibody preparation CAMAL-1 which can be prepared as described by Malcolm et al. (Ex Hematol (1984) 12:539–547); polyclonal or monoclonal preparations of anti-M1 antibody as described by Mew et al. *J Immunol* (1983) 130:1473–1477 and B16G antibody which is prepared as described by Maier et al. *J Immunol* (1983) 131:1843 and Steele et al. *Cell Immunol* (1984) 90:303.

The foregoing list is exemplary and not limiting; once the target tissue is known, antibody specific for this tissue may be prepared by conventional means. Therefore, the invention is applicable to effecting toxicity against any desired target.

Coupling of the target-specific moiety to a CNC-expanded porphyrin of the present invention can be effected by any convenient means known in the art, depending on the nature of the substituents on the CNC-expanded porphyrin moieties. For example, if at least one $R_i$ contains a carboxylic group, a covalent bond to an amino-containing TSM may be effected using a dehydrating agent such as a carbodiimide. A particularly preferred method of covalently binding a CNC-expanded porphyrin to the target-specific moiety is treatment with 1-ethyl-3-(3-dimethylaminopropyl) carbodiimide (EDCI) in the presence of a reaction medium consisting essentially of dimethylsulfoxide (DMSO). A preparation using this preferred procedure is illustrated below. Other dehydrating agents such as dicyclohexylcarbodiimide or diethylcarbodiimide could also be used as well as conventional aqueous and partially aqueous media.

The active moieties of the conjugate may also be coupled through linker compounds which are bifunctional, and are capable of covalently binding each of the two active components. A large variety of these linkers is commercially available, and a typical list would include those found, for example, in the catalog of the Pierce Chemical Co., Rockford, Ill. These linkers are either homo- or heterobifunctional moieties and include functionalities capable of forming disulfides, amides, hydrazones, and a wide variety of other linkages. Other linkers include polymers such as polyamines, polyethers, polyamine alcohols, derivatized to the components by means of ketones, acids, aldehydes, isocyanates, or a variety of other groups.

The techniques employed in coupling the active moieties of the conjugate include any conventional means and the method for coupling does not form part of the invention.

Use of the invention Compounds in PDT and Other Applications

The invention compounds can be used in photodynamic therapy protocols analogous to those known for porfimer sodium and the BPDs. Thus, the compounds can be used to destroy or impair the functioning of unwanted cells or tissues or to inactivate pathogens such as bacteria and viruses.

Examples of target cells and tissues for which PDT is useful include, but are not limited to, tumors, including blood tumors, malignant bone marrow, virally-infected blood cells or bone marrow, dysplastic cells or tissues, sites of inflammation or infection, hyperproliferative tissue such as psoriatic plaque or papillomavirus lesions (warts) or neointimal hyperplasia lesions, hypervascularization such as portwine stains and hemangiomas, atherosclerotic plaque, hair follicles, free viruses, bacteria, protozoa or other pathogenic parasites.

Pathogens that may be adversely affected by PDT include certain viruses, bacteria, protozoa and other pathogenic parasites. Viruses, for example, include enveloped viruses such as human cytomegaloviruses, Epstein-Bart virus, Marek's disease herpes virus, human herpes simplex viruses, varicella-zoster virus, members of the family Poxviridae, members of the family Hepadnaviridae such as human hepatitis A virus (HAV), human hepatitis B virus (HBV) and non-A, non-B hepatitis viruses, including human hepatitis C virus, members of the family Orthomyxoviridae such as influenza virus types A, B and C, members of the family Retroviridae such as human T cell leukemia viruses, human immunodeficiency viruses, and members of the family Flaviviridae such as tick-borne encephalitis virus or yellow fever virus.

Illustrative parasites include *Plasmodium malariae, P. falciparum, P. ovale, P. vivax* and *Trypanosoma cruzi.* Bacteria include *Bacillus subtilis, Streptococcus faecalis,* Pseudomonas spp., Mycobacterium spp. and other opportunistic organisms treatable by photodynamic activation.

The manner of use of the invention compounds in these contexts follows procedures that are established in the art. The choice of wavelength absorption for the CNC-expanded porphyrin used in a particular technique may be influenced by the nature of the use. For example, where the target tissue is in a context with a number of interfering materials such as those found in the blood, it is advantageous to use CNC-expanded porphyrins which have wavelength absorptions not shared with these contaminants. On the other hand, for treatment of superficial target tissues, this consideration is not as relevant. Thus, the presence or absence of alternative compounds capable of absorbing light in the environment to be irradiated with light is taken into consideration in choosing an appropriate member of the class of CNC-expanded porphyrins of the invention and in the choice of wavelength.

In addition to their use in photodynamic therapy, the compounds of the invention may be used for diagnosis in a manner analogous to that for porphyrins per se. The CNC-expanded porphyrins, like the porphyrins themselves, are capable of fluorescence when excited by light of an appropriate wavelength. As the CNC-expanded porphyrins, like the porphyrins themselves, will home to certain target tissues, such as atherosclerotic plaques, tumors, and the like. If appropriate, the invention compounds can be provided with target-specific moieties to assure this "homing". The compounds of the invention may thus be allowed to accumulate in such target tissues or cells if present, and these tissues or cells may be detected or localized by detecting the fluorescence.

In addition, the compounds of the invention may include radioisotopes either as covalently bonded substituents or in the metalated complexes so that the invention compounds can be located by radio- or scintigraphic imaging.

Certain metal ions also provide the compounds of the invention with the ability to serve as MRI contrast agents. These contrast agents are used conventionally in obtaining MRI scans with enhanced readability.

Preparation of the Invention Compounds

A number of strategies may be employed to effect the CNC linkage of the invention. A single CNC linkage may be formed, for example, by reacting a pyrrole substituted in the 2-position with a carboxylic acid moiety with a pyrrole substituted in the 2-position with aminomethyl. This general method for forming the CNC linkage is shown in Reaction Scheme 1.

Reaction Scheme 1

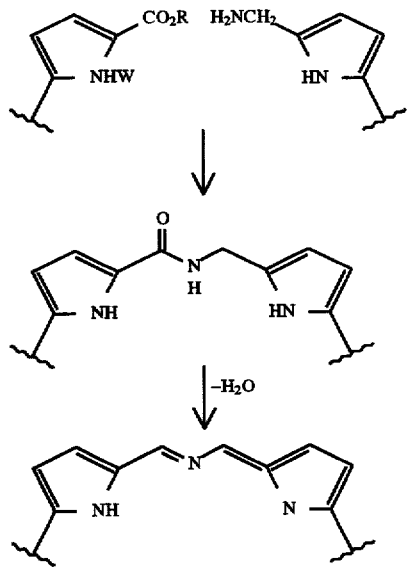

As shown, conventional amide formation is followed by dehydration to form the CNC linkage of the invention. The CNC linkage is stabilized by its inclusion in the resonance system of the aromatic expanded porphyrin nucleus, as is seen with pyrrole.

An additional approach is illustrated by Reaction Scheme 2 which effects the linkage by condensation of two cyano groups, each linked to the 2-position of an adjoining pyrrole.

Reaction Scheme 2

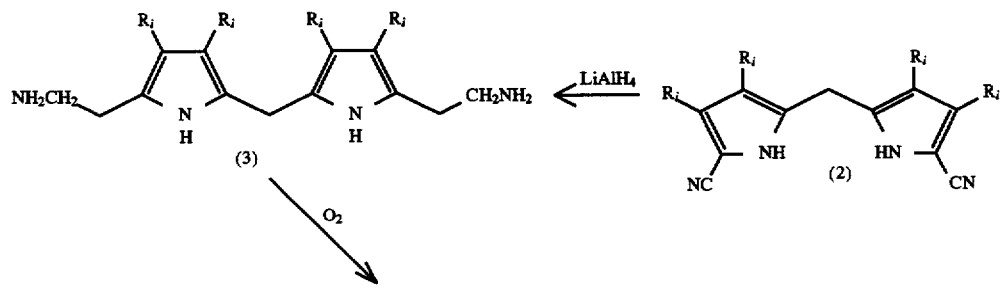

-continued
Reaction Scheme 2

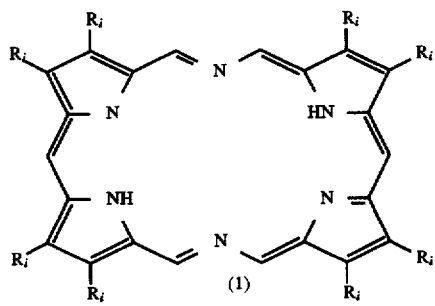
(1)

As shown in Reaction Scheme 2, the cyano-substituted dipyrrole in this case is first reduced with lithium aluminum hydride and then treated with oxygen to form the resultant CNC linkage. The reduced compound (3) is partly ionized and the ionized form combines with the compound of formula (3) in the presence of $O_2$ to give the product (1).

An alternative to Reaction Scheme 2 is shown in Reaction Scheme 3. Instead of treating the lithium aluminum hydride-reduced dicyano compound with oxygen; DDQ in methylene chloride and THF are used.

Reaction Scheme 3'

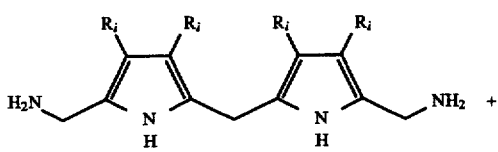

Reaction Scheme 3

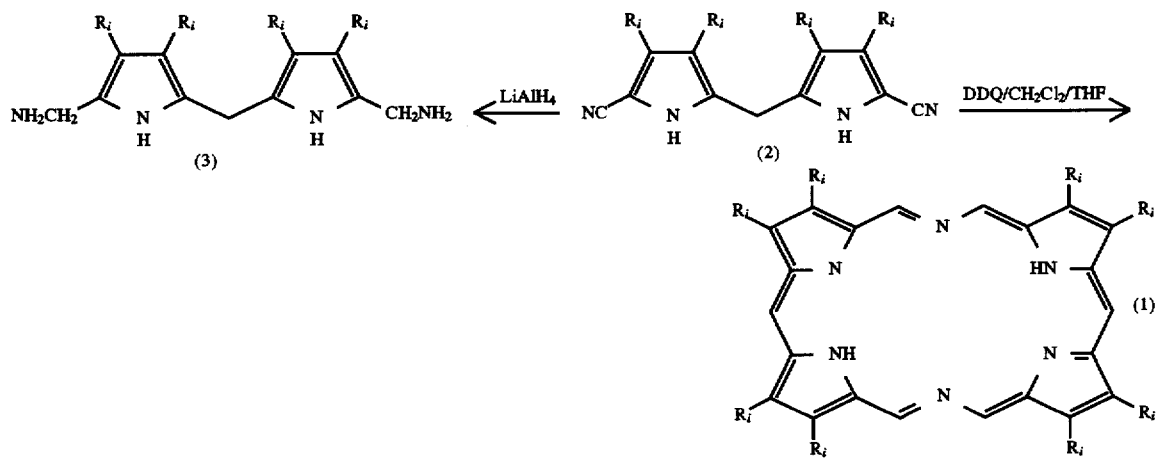

It will be apparent from Reaction Scheme 3 that rather than starting with the bisnitrile, the starting materials could also comprise the bisaminomethyl-derived dipyrromethane shown as formula (3). This starting material is especially advantageously employed in obtaining asymmetric forms of the porphocyanines of formula (1a). This is illustrated in Reaction Scheme 3' which illustrates the condensation of two different "halves" of the porphocyanine nucleus to obtain the desired asymmetric product. Of course, the two symmetric products are also formed, but these are readily separated from the desired asymmetric product using standard chromatographic techniques.

-continued
Reaction Scheme 3'

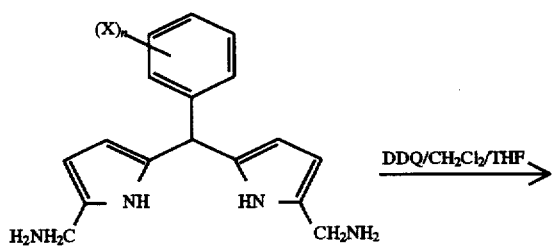

Reaction Scheme 3'

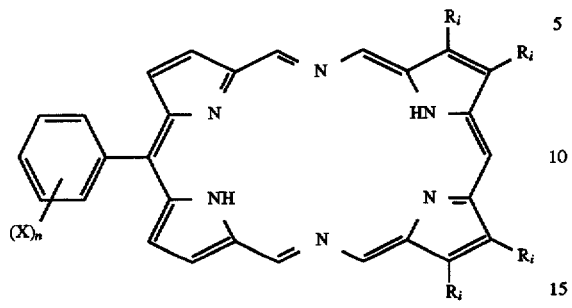

In another variant of Reaction Scheme 3', rather than condensing two diaminomethyldipyrromethanes as shown, the bisaldehyde (which can be obtained as an intermediate in Reaction Scheme 5 below) is added. This facilitates the production of asymmetric forms of the porphocyanines in which the nature of $R_{1a}$, $R_{1b}$, $R_{4a}$ and $R_{4b}$ (as well as $R_{1c}$) can be different from $R_{2a}$, $R_{2b}$, $R_{3a}$, $R_{3b}$ and $R_{3c}$. Thus, the substituents on the compound of formula (3) shown in Reaction Scheme 3 can be different from those on the dialdehyde and a single asymmetric product is obtained.

In the alternative, a dialdehyde form of the dipyrrole intermediate can be condensed directly using ammonia in ethanol as shown in Reaction Scheme Reaction Scheme 4

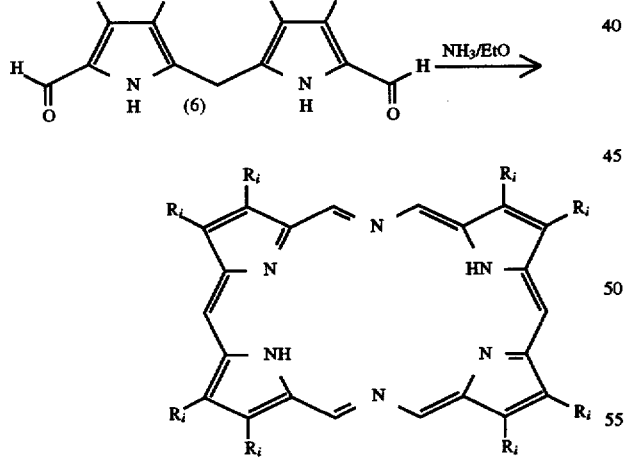

The dipyrrole moiety containing two cyano groups for condensation in Reaction Schemes 2 or 3, or the dialdehyde for condensation in Reaction Scheme 4 can be obtained as shown in Reaction Scheme 5.

Reaction Scheme 5

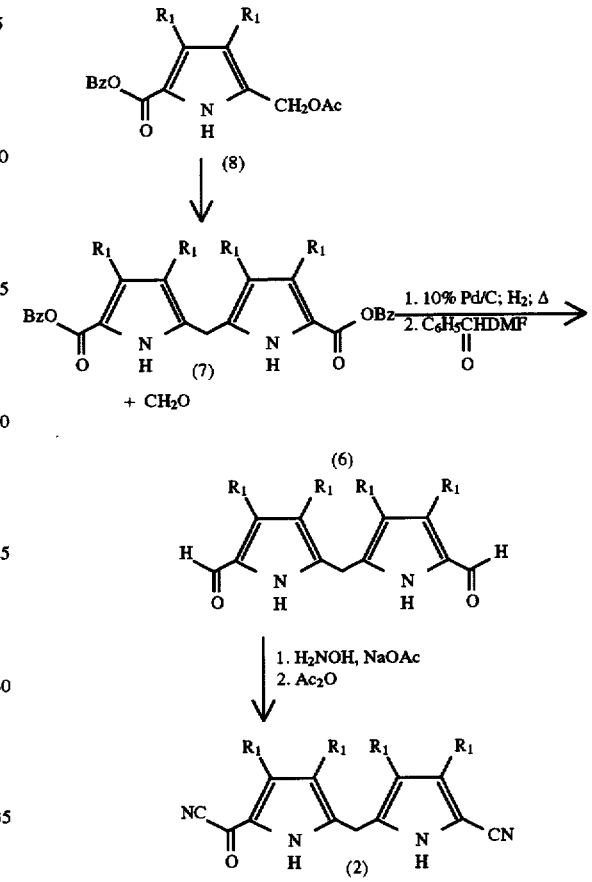

As shown, the dipyrrole is formed by the condensation of two molecules of 2-benzoyl carbonyl-4-acetoxylmethyl pyrrole. The resulting dipyrrole is converted to the corresponding dialdehyde and converted to the cyano derivative using standard reagents.

Finally, Reaction Scheme 6 shows an additional alternative for obtaining the dicyano intermediate typified by formula (2). The dicyano compound can then be converted to the appropriate porphocyanine using the approaches set forth above in Reaction Schemes 2 or 3.

Reaction Scheme 6

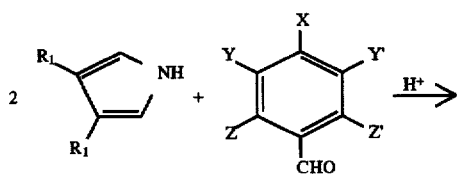

-continued
Reaction Scheme 6

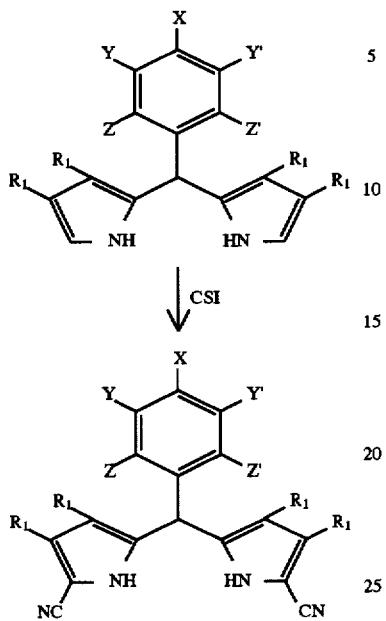

In the initial step of Reaction Scheme 6, benzaldehyde optionally substituted with 1–5 independently selected substituents is used to form the meso bridge between the two condensed pyrrole nuclei. However, other aldehydes can also be used, including formaldehyde and simple alkyl aldehydes such as acetaldehyde, butyraldehyde, hexylaldehyde, and the like. In addition, other aryl aldehydes, such as 1-naphthylaldehyde, can also be used. In the second step, chlorosulfonyl isocyanate ($ClSO_2N=C=O$; CSI) in a polar aprotic solvent, such as DMF, derivatizes the pyrrole nuclei so as to contain the desired cyano groups in the 5-positions. The specific components shown in Reaction Scheme 6 are intended to be illustrative, not limiting.

Concerning more details related to Reaction Scheme 5, the tetraethyl-substituted dicyanodipyrrole is used as an illustration as follows: The starting material, 2-benzyloxycarbonyl-3,4-diethyl-5-methyl pyrrole (not shown) in glacial acetic acid is treated with lead tetraacetate. Ethylene glycol is added to reduce any remaining Pb(IV). Water is added and the 5-acetoxymethyl-2-benzyloxycarbonyl-3,4-diethylpyrrole, shown as the starting material in Reaction Scheme 5, is collected by filtration and washed with additional water.

The 5-acetoxymethyl-2-benzyloxycarbonyl-3,4-diethylpyrrole is added to acetic acid in water and heated. The solid product, is precipitated as large chunks when the foregoing solution cools to room temperature. Water is added and the product is collected by filtration and then washed with additional water. The filtrate is extracted with $CH_2Cl_2$ and then evaporated to produce a solid product. The solid products are combined, and then recrystallized from a solution of $CH_2Cl_2$ and hexanes to obtain 5,5'-bis (benzyloxycarbonyl)-3,3'4,4'-tetraethyl-2,2'-dipyrromethane.

This product is dissolved in tetrahydrofuran (THF) and stirred under hydrogen in the presence of Pd/C and triethylamine. After the catalyst is filtered through celite, the filtrate is evaporated to dryness, dissolved in N,N-dimethylformamide and heated to boiling under argon. The solution is chilled and an excess of chilled benzoyl chloride is added. The reaction mixture is stirred and the solid product collected by filtration. The solid product is added to water and basified using $NaHCO_3$ and heated to 60° C. The pale yellow product, 3,3',4,4'-tetraethyl-5,5'-diformyl-2,2'-dipyrromethane, crystallizes from the solution and is filtered and washed with water.

This product is dissolved in ethanol and bubbled with argon; hydroxylamine hydrogen chloride and sodium acetate are added. This mixture is heated under argon and the solvent is removed and the product dried overnight in vacuo. The resulting bisoxime is dissolved in acetic anhydride and saturated with argon to generate the crude bisnitrile product, which is obtained as a black solid after removal of acetic anhydride and dried under vacuum. The product shown as the end product of Reaction Scheme 5 is purified by silica gel column with 0.5% methanol in $CH_2Cl_2$, followed by an alumina column with 10–20% EtOAc. Evaporation of the solvent yields the 3,3'4,4'-tetraethyl-5,5'-cyanodipyrromethane as pale pink crystals.

The product obtained above can then be converted to the desired corresponding porphocyanine as illustrated in Reaction Scheme 2. The 3,3'4,4'-tetraethyl-5,5'-cyanodipyrromethane in anhydrous THF is added to a THF suspension of $LiAlH_4$ under nitrogen at 0° C. The mixture is stirred and water is added to quench the reaction and the precipitate is filtered off. The golden colored solution is transferred to a two-neck flask containing equimolar portions of $Pb(SCN)_2$ and anhydrous sodium sulphate. Anhydrous methanol is added and the mixture is brought to reflux. The color gradually changes from purple to dark green. The reaction is stopped and air is bubbled slowly through the solution. The crude product was dissolved in methylene chloride and the solid was filtered off. The volume of the green solution is reduced to approximately 5 ml and then charged on an alumina column and eluted with ethylacetate in $CH_2Cl_2$. The bright green eluent containing the porphocyanine is collected and evaporated to dryness.

If Reaction Scheme 3 is to be followed in order to obtain the desired porphocyanine, the conduct of this sequence of reactions may be illustrated, again using the tetraethyl-substituted dipyrromethane as an example, as follows:

The 3,3'4,4'-tetraethyl-5,5'-cyanodipyrromethane in anhydrous THF is added to a THF suspension of $LiAlH_4$ under nitrogen at 0° C. The mixture is stirred and water is added to quench the reaction and the precipitate is filtered off. A ten-fold excess of 2,3-dichloro-5,6-dicyano-1,4-benzoquinone (DDQ) in a $THF/CH_2Cl_2$ suspension under nitrogen at 0° C. is added to the 3,3'4,4'-tetraethyl-5,5'-bisaminomethyl-2,2'-dipyrromethane in anhydrous THF/$CH_2Cl_2$. The solution turns dark green immediately. The crude product is dissolved in methylene chloride and the solid filtered off. The volume of the green solution is reduced to approximately 5 ml and then charged on an alumina column and eluted with ethylacetate in $CH_2Cl_2$. The bright green eluent containing the porphocyanine is collected and evaporated to dryness. A significant increase in yield is obtained from this synthetic process as compared to the yield obtained via air oxidation.

To prepare the product from the bisaldehyde and the bisnitrile, the 3,3'4,4'-tetraethyl-5,5'-cyanodipyrromethane, for example, is dissolved in THF and added to a THF suspension of $LiAlH_4$. The resulting mixture is stirred and water is added. A solid product forms which is filtered off. The bisamine product is obtained after evaporation of the solvent by drying under vacuum. The bisamine is dissolved in anhydrous methanol and bisaldehyde is added. The solution is bubbled and brought to reflux with nitrogen. Lead thiocyanate Pb(SCN$_2$)) is added and the solution is refluxed. Oxygen gas is bubbled through the solution at room temperature. After evaporation of the solvent, the crude porphocyanine product is dried under vacuum. The product is purified by Al$_2$O$_3$ column with ethyl acetate in CH$_2$Cl$_2$. The green eluent is collected and concentrated. Crystals of the product porphocyanine are obtained after evaporation of the solvent.

The conduct of still another alternative, Reaction Scheme 4, is illustrated as follows. An illustrative dialdehyde (6) 3,3'4,4'-tetraethyl-5,5'-diformyl-2,2'-dipyrromethane is suspended in dry EtOH. The resulting ethanol solution is chilled at 0° C. and ammonia gas is bubbled through it. The flask is then placed in an oil bath at 60° C. for 72 hours. The reaction is stopped and cooled at 0° C. Ethanol is removed on the roto-vap, the residue is chromatographed on neutral Alumina with dichloromethane. This greatly simplified synthetic process produces high yields of the porphocyanine.

In order to prepare the alternative embodiments of the CNC-expanded porphyrins of the invention, appropriate modifications of the Reaction Schemes leading to the porphocyanine compounds per se are employed as would generally be understood in the art. For example, to obtain the CNC-expanded porphyrin of formula (1b), the condensation reactions set forth in Reaction Schemes 2 or 3 are employed using as starting material 2,5-dicyanopyrrole. To obtain the embodiments of formula (1c), the condensation of the diaminomethyl derivative with a dialdehyde is preferably employed. The dialdehyde of the dipyrrole methane along with the diaminomethylated pyrrolyl pyrrole are reacted to form the desired product. For production of the compounds of formula (1d), and (1e), the CNC bonds are formed as described above from the relevant tetrapyrrole starting material. Such modifications are well understood by ordinary practitioners and conventional means to synthesize these alternatives may be employed.

Administration and Use

The invention compounds or conjugates thereof are formulated into pharmaceutical compositions for administration to the subject using techniques known in the art generally. A summary of such pharmaceutical compositions may be found, for example, in *Remington's Pharmaceutical Sciences* (Mack Publishing Co., Easton, Pa., latest edition).

The invention compounds and their conjugates are administered systemically for some indications, preferably by injection. Injection may be intravenous, subcutaneous, intramuscular, or even intraperitoneal. Injectables can be prepared in conventional forms, either as liquid solutions or suspensions, solid form suitable for solution or suspension in liquid prior to injection, or as emulsions. Suitable excipients are, for example, water, saline, dextrose, glycerol and the like. Of course, these compositions may also contain minor amounts of nontoxic, auxiliary substances such as wetting or emulsifying agents, pH buffering agents and so forth.

Systemic administration can also be implemented through implantation of a slow release or sustained release system, by suppository, or, if properly formulated, orally. Formulations for these modes of administration are well known in the art, and a summary of such methods may be found, for example, in *Remington's Pharmaceutical Sciences* (supra).

If the treatment is to be localized, such as for the treatment of superficial tumors or skin disorders, the compounds may be topically administered using standard topical compositions involving lotions, suspensions, pastes, or creams.

The quantity of compound to be administered depends on the choice of active ingredient, the condition to be treated, the mode of administration, the individual subject, and the judgment of the practitioner. Depending on the specificity of the preparation, smaller or larger doses may be needed. Dosages in the range of about 0.05–10 mg/kg are suggested for systemic administration. Dosages in the range of about 0.01–20% concentration of active ingredient, preferably 1–5%, are suggested for topical administration. A total daily dosage in the range Of about 10–300 mg are suggested for oral administration. The foregoing ranges are merely suggestive, as the number of variables in regard to an individual treatment regime is large and considerable excursions from these recommended values are expected.

The radioimaging (scintigraphic imaging) method of the present invention is practiced by injecting an individual parenterally with an effective amount of the porphocyanine radioimaging agent. By parenterally is meant, e.g., intravenously, intraarterially, intrathecally, interstitially or intracavitarily. It is contemplated that an individual will receive a dosage of from about 1 mCi to 50 mCi of the radioimaging agent, the amount being a function of the particular radioisotope and mode of administration. For intravenous injection, the amount are normally: about 10–40 mCi, preferably about 20 mCi of Tc-99m; about 2–5 mCi, preferably about 4 mCi of In-111 or Ga-67.

The radioimaging agent is conveniently provided as an injectable preparation, preferably a sterile injectable preparation for human use, for targeting the agent to diseased tissue or cells, preferably comprising: a sterile injectable solution containing an effective amount of the radiolabeled agent in a pharmaceutically acceptable sterile injection vehicle, preferably phosphate buffered saline (PBS) at physiological pH and concentration. Other pharmaceutically acceptable vehicles may be utilized as required for the site of parenteral administration.

A representative preparation to be parenterally administered in accordance with this invention will normally contain about 0.1 to 20 mg, preferably about 2 mg, of radiolabeled agent in a sterile solution.

Once enough isotope has been deposited at the target site, scanning is effected with either a conventional planar and/or SPECT gamma camera, or by use of a hand held gamma probe used externally or internally to localize the inflammation or the lesion. The scintigram is normally taken by a gamma imaging camera having one or more windows for detection of energies in the 50–500 KeV range.

Administration of the contrast agents for magnetic resonance imaging (MRI) is effected in an analogous method to administration for radioimaging except that the compounds of the invention will be in the metalated forms employing paramagnetic ions. Normally the signal generated is correlated with the relaxation times of the magnetic moments of protons in the nuclei of the hydrogen atoms of water molecules in the region to be imaged. The magnetic resonance image contrast agent acts by increasing the rate of relaxation, thereby increasing the contrast between water molecules in the region where the imaging agent accretes and water molecules elsewhere in the body. However, the effect of the agent is to increase both $T_1$ and $T_2$, the former resulting in greater contrast, while the latter results in lesser contrast. Accordingly, the phenomenon is concentration dependent, and there is normally an optimum concentration of a paramagnetic species for maximum efficiency. The optimum concentration will vary with the particular agent used, the locus of imaging, the mode of imaging, i.e., spin-echo, saturation-recovery, inversion-recovery and for various other strongly $T_1$ dependent or $T_2$ dependent imaging techniques, and the composition of the medium in which the agent is dissolved or suspended. These factors, and their relative importance are known in the art. See, e.g., Pykett, *Scientific American* (1982) 246:78, and Runge et al., *Am J Radiol* (1987) 141:1209.

The MRI method of the invention is practiced by injecting an individual parenterally with an effective amount of the MRI contrast agent of the invention which includes a metallic element such as gadolinium. It is contemplated that an individual will receive a dosage of contrast agent sufficient to enhance the MRI signal at the targeted site by at least about 20%, preferably 50–500%, the amount being a function of the particular paramagnetic species and the mode of administration.

A contrast agent within the present invention is conveniently provided as an injectable preparation for use, preferably a sterile injectable preparation for human use, for targeting an MRI agent to diseased tissues or cells, preferably comprising: a sterile injectable solution containing an effective amount of the contrast agent in a pharmaceutically acceptable sterile injection vehicle, preferably phosphate buffered saline. Other conventional pharmaceutically acceptable vehicles for parenteral administration may be utilized as required for the site of parenteral administration.

A representative preparation to be parenterally administered in accordance with this invention will normally contain about 0.1 to 20 mg, preferably about 2 mg of contrast agent, in a sterile solution.

EXAMPLES

The following examples are intended to illustrate the invention but not to limit its scope.

Example 1

Synthesis of an Octaethyl Porphocyanine

Reaction Scheme 5 followed by Reduction and imine Formation

This example describes the conduct of Reaction Scheme 5 to prepare both the bisaldehyde and the bisnitrile dipyrrole intermediates. It also illustrates the condensation of the bisnitrile with the bisaldehyde to obtain the CNC linkages of formula (1a).

Lead tetraacetate (18.2 g, 0.041 mole) was added to a stirred solution of 2-benzyloxycarbonyl-3,4-diethyl-5-methyl pyrrole (10.1 g, 0.037 mole) in 60 ml glacial acetic acid. The mixture was warmed briefly to 60° C. Ten ml of ethylene glycol was added to reduce any remaining Pb(IV). Twenty ml of water was added and the 5-acetoxymethyl-2-benzyloxycarbonyl-3,4-diethylpyrrole (8) was collected by filtration and washed with additional water. The 5-acetoxymethyl-2-benzyloxycarbonyl-3,4-diethylpyrrole was added to 80% acetic acid in 100 ml water and heated at 100° C. for one hour. The solid product precipitated as large chunks when the foregoing solution cooled to room temperature. One hundred ml of water was added and the product was collected by filtration and then washed with additional water. The filtrate was extracted with $CH_2Cl_2$ and then evaporated to produce a solid product. The solid products were combined, and then recrystallized from a solution of $CH_2Cl_2$ and hexanes to obtain 5,5'-bis(benzyloxycarbonyl)-3,3'4,4'-tetraethyl-2,2'-dipyrromethane (7).

Yield: 6.6 g, 67.4%

Mol. Wt. Calcd. for $C_{33}H_{38}O_4N_2$: 526.2831

High resolution MS: 526.2835

$^1$H NMR in $CDCl_3$: 1.05 (t, 6H), 1.12 (t, 6H), 2.43 (q, 4H), 2.75 (q, 4H), 3.85 (s, 2H), 5.25 (s, 4H), 7.28–7.40 (m, 10H), 8.70 (br s, 2H).

The above product (8.1 g, 0.015 mole) in 200 ml tetrahydrofuran (THF) was stirred under hydrogen at atmospheric pressure and room temperature overnight in the presence of 0.4 g 10% Pd/C and 5 drops of triethylamine. After the catalyst was filtered through celite, the filtrate was evaporated to dryness on a roto-vap resulting in dicarboxylic acid. The dicarboxylic acid was dissolved in 100 ml N,N-dimethylformamide and heated to boiling under argon for one and one-half hours. The solution was then chilled on ice and an excess of chilled benzoyl chloride (7.2 ml) was added drop-wise and the reaction mixture was stirred for 2 hours at 5° C. and the solid product collected by filtration. The solid product was added to 50 ml water and basified using $NaHCO_3$. The solution was heated and held at 60° C. for one hour. The pale yellow product which crystallized from the solution was filtered and then washed with water to obtain 3,3',-4,4'-tetraethyl-5,5'-diformyl-2,2'-dipyrromethane (6).

Yield: 3.4 g, 70.0%

Mol. Wt. Calcd. for $C_{19}H_{26}N_2O_2$: 314.1994

High resolution MS: 314.1994

$^1$HNMR in $CDCl_3$: 1.10 (t, 6H), 1.25 (t, 6H), 2.50 (q,4H), 2.70 (q, 4H), 4.00 (s, 2H), 9.55 (s, 2H), 10.90 (s, 2H).

This product (1.03 g, 0.0033 mole) in 300 ml ethanol was bubbled with argon for 20 minutes. Hydroxylamine hydrogen chloride (0.51 g, 0.0073 mole) and sodium acetate (1.20 g, 0.015 mole) were added. This mixture was heated at 60° C. under argon for two and one-half hours. The solvent was removed on a roto-vap and the product dried overnight in vacuo. The bisoxime was dissolved in 5 ml acetic anhydride and saturated with argon for 30 minutes. The crude bisnitrile product (2) was obtained as a black solid after removal of acetic anhydride and dried under vacuum overnight. The product was purified by silica gel column (40 g) with 0.5% methanol in $CH_2Cl_2$, followed by an alumina column (40 g) with 10–20% EtOAc. Evaporation of the solvent yielded pale pink crystals of 3,3'4,4'-tetraethyl-5,5'-cyanodipyrromethane (2).

Yield: 0.43 g, 42%

Mol. Wt. Calcd. for $C_{19}H_{24}N_4$: 308.2001

High resolution MS: 308.2002.

$^1$H NMR in $CDCl_3$: 1.10 (t, 6H), 1.25 (t, 6H), 2.45 (q, 4H), 2.60 (q, 4H), 3.90 (s, 2H), 8.45 (s, 2H).

This product (2) (0.053 g, $1.7 \times 10^{-4}$ mole) was dissolved in 10 ml anhydrous THF and added dropwise to a THF suspension of $LiAlH_4$ (0.050 g, $1.5 \times 10^{-3}$ mole) under $N_2$ at 0° C. The resulting mixture was stirred for 30 minutes and two drops of water was added. A solid product formed which was filtered off. The bisamine product was obtained after evaporation of the solvent by drying under vacuum overnight. The bisamine (3) was dissolved in 50 ml anhydrous methanol and bisaldehyde (6) (0.050 g, $1.6 \times 10^{-4}$ was added. The solution was bubbled with $N_2$ for 20 minutes and brought to reflux under $N_2$. Lead thiocyanate ($Pb(SCN_2)$) (0.055 g, $1.7 \times 10^{-4}$ mole) was added and the solution refluxed for 4 hours. Oxygen gas was bubbled through the solution at room temperature overnight. After evaporation of the solvent, the crude porphocyanine product was dried under vacuum overnight. The product was purified by $Al_2O_3$ column (4% water added) with 10% ethyl acetate in $CH_2Cl_2$. The green eluent was collected and concentrated on the roto-vap. Crystals of 2,3,9,10,14,15,21,22-octaethyl porphocyanine (1) were obtained after evaporation of the solvent.

Yield: 19.3 mg, 19.1% macrocycle

Mol. Wt. Calcd. $C_{38}H_{48}N_6$: 588.3941

High resolution MS: 588.3933

$^1$H NMR (300 MHz, $CDCl_3$), −4.50 (bs, 2H), 2.05 (t, 12H), 2.13 (t, 12H), 4.28 (q, 8H), 4.40 (q, 8H), 10.50 (s, 2H), 13.0 (s, 4H).

UV/VIS in $CH_2Cl_2$ 455, 592, 800 nm.

Example 2

Synthesis of an Octaethyl Porphocyanine (Reaction Scheme 2)

This example illustrates the formation of a porphocyanine of formula (Ia) using the condensation procedure shown in Reaction Scheme 2.

3,3'4,4'-tetraethyl-5,5'-cyanodipyrromethane was prepared according to the methodology of Example 1. 0.102 g, $3.3 \times 10^{-4}$ mole of 3,3'4,4'-tetraethyl-5,5'-cyanodipyrromethane in 10 ml anhydrous THF was slowly added to a 20 ml THF suspension of $LiAlH_4$ under $N_2$ at 0° C. The mixture was stirred for 30 minutes and two drops of water were added to quench the reaction. The precipitate was filtered off. The golden colored solution was transferred to a two-neck flask containing equimolar portions of $Pb(SCN)_2$ and anhydrous sodium sulphate. Fifteen ml of anhydrous methanol were added and the mixture was brought to reflux. The color of the solution gradually changed from purple to dark green. The reaction was stopped after four and one-half hours and air was bubbled slowly through the solution overnight. The crude product was dissolved in methylene chloride and the solid was filtered off. The volume of the green solution was reduced to approximately 5 ml and then charged on an alumina column (120 g, 4% water added) and eluted with 10% ethylacetate in $CH_2Cl_2$. Two liters of the bright green eluent containing the porphocyanine was collected and evaporated to dryness.

Yield: 23.4 mg, 24.1%

The spectroscopic data of this compound are identical to the compound prepared in Example 1 above.

Example 3

Synthesis of an Octaethyl Porphocyanine (Reaction Scheme 3)

This example illustrates Reaction Scheme 3. 3,3'4,4'-tetraethyl-5,5'-cyanodipyrromethane (2) was prepared according to the methodology of Example 1. A ten-fold excess of 2,3-dichloro-5,6-dicyano-1,4-benzoquinone (DDQ) was added to 69 mg of 3,3'4,4'-tetraethyl-5,5'-cyanodipyrromethane in 10 ml anhydrous THF. The resulting solution turned dark green immediately. The residue was chromatographed according to the methodology of Example 2. A significant increase in yield was obtained when compared to air oxidation.

Yield: 32 mg.

The spectroscopic data of this compound are identical to the compound prepared in Example 1 above.

Example 4

Synthesis of Porphocyanine (Reaction Scheme 4)

This example illustrates Reaction Scheme 4. The dialdehyde was prepared according to the methodology of Example 1. 25 mg of 3,3'4,4'-tetraethyl-5,5'-diformyl-2,2'-dipyrromethane (6) was suspended in 30 ml dry EtOH. The resulting ethanol solution was chilled at 0° C. and ammonia gas was bubbled through it for 30 minutes. The gas inlet was then removed and the flask placed in an oil bath at 60° C. for 72 hours. The reaction was stopped and cooled at 0° C. Ethanol was removed on the roto-vap and the residue was chromatographed on neutral Alumina (4% $H_2O$ added) with dichloromethane.

Yield: 4.6 mg, 20%

The spectroscopic data of this compound are identical to the compound prepared in Example 1 above. Another 1.5 mg of product was obtained from the oxidation of the more polar component by DDQ.

Example 5

Synthesis of 2,2'-bis cyano meso aryl dipyrromethanes

This example illustrates Reaction Scheme 6.

General procedure: 250 ml round bottomed flask is charged with methanol (115 ml), pyrrole (10 ml; 105 mmol) and p-toluene sulfonic acid (2.15 g; 11.5 mmol). To this stirred solution is added a solution of the aromatic aldehyde (11.25 mmol) in methanol (30 ml) over 100 min. After this time the reaction is poured into water (350 ml) and extracted with dichloromethane (3×150 ml). The organic phase is washed with brine (3×200 ml) and dried over anhydrous potassium carbonate. Evaporation of solvent in vacuo followed by flash chromatography (silica gel; 100 g) of the residue gives the meso aryl dipyrromethane.

The meso aryl dipyrromethane (0.32 mmol) is dissolved in N,N-dimethylformamide (5 ml), this solution is then diluted with acetonitrile (5 ml) and the stirred mixture is cooled to −78° C. To the cooled mixture, under an atmosphere of $N_2$ is added dropwise a solution of chlorosulfonyl isocyanate (1.42 mmol) in acetonitrile (3 ml). The mixture is stirred at −78° C. for 1 hour then at −40° C. for a further hour before being allowed to rise to room temperature. The reaction mixture is poured into a mixture of 5% aqueous sodium hydrogen carbonate 15 ml), aqueous potassium hydroxide (3M; 2.7 ml) and ice then diluted with brine (200 ml) and extracted with dichloromethane (3×50 ml). The organic phase ms dried over anhydrous potassium carbonate, the solvent evaporated in vacuo and the residue chromatographed on silica gel to give the 2,2'-bis cyano meso aryl dipyrromethane.

Example 6

Condensation of 2,2'-bis cyano meso aryl dipyrromethanes to Prepare Symmetric Porphocyanines This illustrates the method of Reaction Scheme 3 where at least one $R_{ic}$ is aryl.

General method: A solution of 2,2'-bis cyano meso aryl dipyrromethane (0.124 mmol) in tetrahydrofuran (5 ml) is added dropwise to a stirred suspension of lithium aluminum hydride (1.3 mmol) in tetrahydrofuran (10 ml) under an atmosphere of $N_2$ at 0° C. The reduction is followed by thin layer chromatography (silica gel), eluting with 10% ethyl acetate in dichloromethane until complete, then excess $LiAlH_4$ is quenched with water, dichloromethane (15 ml) is added, and the mixture is filtered. The filtrate is dried over anhydrous sodium sulfate and the solvent evaporated in vacuo. The residue is redissolved in dry dichloromethane (100 ml) and to the stirred solution is added, dropwise, a solution of dichlorodicyanobenzoquinone (5 equivalents) in toluene (5 ml). The oxidation is followed by UV-vis spectroscopy and when no further porphocyanine formation is detected the reaction mixture is filtered through a plug of neutral alumina to remove excess DDQ, and the solvent is evaporated in vacuo. The crude diphenyl porphocyanine is purified by chromatography on alumina.

Example 7

Application of the Methods of Examples 5 and 6

In the examples below which describe various porphocyanines, the following numbering system will be used:

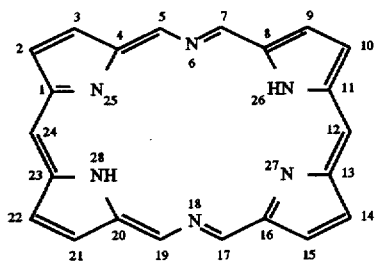

Using the Method of Examples 5 and 6, the following were prepared.

1. 12,24-Diphenyl porphocyanine: 1 g benzaldehyde gives 732 mg (35%) meso phenyl dipyrromethane after chromatography (silica gel; 10% hexane in dichloromethane). 500 mg meso phenyl dipyrromethane gives 195 mg (32%) 2,2'-bis cyano meso phenyl dipyrromethane after chromatography (silica gel; 5% acetonitrile in dichloromethane). 100 mg 2,2'-bis cyano meso phenyl dipyrromethane gives 28 mg (29% 1,11-diphenyl porphocyanine after chromatography (60–325 mesh neutral alumina; 10% ethyl acetate in dichloromethane).

Spectroscopic data: $^1$H NMR (CDCl$_3$) δ7.92 (m, 6H), 8.44 (m, 4H), 9.38 (d, j=5.7 Hz, 4H), 9.8 (d, J=5.7 Hz, 4H), 12.95 (s, 4H); UV-vis: λ452,598,640,814 nm in CH2Cl$_2$; HRMS (EI) for C$_{34}$H$_{24}$N$_6$(M$^+$) calcd. 516.2062, found 516.2058.

2. 12,24-Di(3',4',5'-trimethoxyphenyl)porphocyanine: 2.21 g 3,4,5-trimethoxybenzaldehyde gives 1.147 g (33%) meso (3,4,5-trimethoxyphenyl)dipyrromethane after chromatography (silica gel; 3% acetone in dichloromethane). 1 g meso (3,4,5-trimethoxyphenyl)dipyrromethane gives 460 mg (40%) w,w'-bis cyano meso (3,4,5-trimethoxyphenyl) dipyrromethane after chromatography (silica gel; 10% ethyl acetate in dichloromethane). 100 mg 2,2'-bis cyano meso (3,4,5-trimethoxyphenyl)dipyrromethane gives 31 mg (32% 1,11-di(3'4',5'-trimethoxyphenyl)porphocyanine after chromatography (60–325 mesh neutral alumina; ethyl acetate/ bichloromethane (1:1)).

Spectroscopic data: $^1$H NMR (CDCl$_3$) δ4.1 (s, 12H), 4.25 (s, 6H), 7.67 (s, 4H) 9.44 (d, J=4.8 Hz, 4H) 9.8 (d, J=4.8 Hz, 4H), 12.95 (s, 4H); UV-vis: λ460,602,644,818 nm in CH$_2$Cl$_2$; HRMS (EI) for C$_{40}$H$_{36}$N$_6$O$_6$ (M$^+$) calcd. 696.2696, found 696.2690.

3. 12,24-Di(pentafluorophenyl)porphocyanine:

2.22 g pentafluorobenzaldehyde gives 1.48 g (42%) meso (pentafluorophenyl)dipyrromethane after chromatography (silica gel; 25% hexane in dichloromethane). 200 mg meso (pentafluorophenyl) dipyrromethane gives 89 mg (38% 2,2'-bis cyano meso (pentafluorophenyl)dipyrromethane after chromatography (silica gel; 5% ethyl acetate in dichloromethane). 89 mg 2,2'-bis cyano meso (pentafluorophenyl)dipyrromethane gives 23 mg (28%) 1,11-di(pentafluorophenyl)porphocyanine after chromatography (60–325 mesh neutral alumina; 5% acetone in dichloromethane).

Spectroscopic data: $^1$H NMR ((D$_3$C)$_2$CO) δ9.55 (dd, J$_1$=15.22 Hz, J$_2$=4.15 Hz, 4H), 10.1 (d, J=4.15 Hz, 4H), 13.24 (s, 4H); $^{19}$F NMR ((D$_3$C)$_2$CO) 60.53, 60.92, 61.45 referenced to F$_3$CCOOH; UV-vis: 442,582,624,814 nm in acetone; HRMS (EI) for C$_{34}$H$_{14}$N$_6$F$_{10}$ (M$^+$) calcd. 696.1120, found 696.1124.

Example 8

Condensation to Obtain Asymmetric Porphocyanines

This example employs the method of Reaction Scheme 3.

General procedure: Two differently substituted 2,2'-bis cyano dipyrromethanes (0.1 mmol) are dissolved in dry tetrahydrofuran (5 ml) and the two solutions are mixed. The mixed solution is added dropwise to a suspension of LiAlH$_4$ in dry THF (10 ml) under an atmosphere of N$_2$ at 0° C. The reduction is followed by TLC and, when complete, excess LiAlH$_4$ is quenched with water and dichloromethane (5 ml) is added. The resulting slurry is gravity filtered and the filtrate is dried over anhydrous sodium sulfate. Evaporation of solvent in vacuo, followed by redissolution in dichloromethane (20 ml) gave a golden solution. To this solution is added, dropwise, a solution of DDQ (5 equivalents) in toluene (5 ml). The oxidation is followed by UV-vis spectroscopy and, when no further porphocyanine formation is seen, the reaction mixture is filtered through a plug of neutral alumina. Evaporation of the solvent from the filtrate gives the crude mixture of porphocyanines which are resolved by chromatography.

Example 9

Application of the Method of Example 8

Using the method of Example 8, the following was prepared:

12-Phenyl-2,3,21,22-tetraethyl porphocyanine 51 mg 2,2'-bis cyano meso phenyl dipyrromethane+58 mg 2,2'-bis cyano 3,3'4,4'-tetraethyl dipyrromethane gives 48 mg of crude mixed porphocyanine. After chromatography (C$_{18}$ reversed phase; 20% 0.1% aqueous trifluoroacetic acid in 0.1% trifluoroacetic acid/acetonitrile) 21.7 mg (21%) of the title compound is isolated.

Spectroscopic data: $^1$H NMR (CDCl$_3$) $^1$H NMR (CDCl$_3$) 2.05 (t, J=7.5 Hz, 3H), 2.07 (t, J=7.5 Hz, 3H), 4.21 (q, J=7.5 Hz, 2H), 4.32 (q, J=7.5 Hz, 2H), 7.88 (m, 3H), 8.41 (m, 2H), 9.31 (d, J=4.5 Hz, 2H), 9.7 (d, J=4.5 Hz, 2H), 10.3 (s, 1H), 12.72 (s, 2H), 12.96 (s, 2H); UV-vis: λ456,592,632,804 nm in CH$_2$Cl$_2$; HRMS (EI) for C$_{36}$H$_{36}$N$_6$ (M$^+$) calcd. 552.3001, found 552.2996.

Example 10

12,24-Diphenyl β-alkyl porphocyanine

This general procedure, encompassing part of Reaction Scheme 5 and Reaction Scheme 2, begins with the bis carboxy dipyrromethane: 2,2'-bis carboxy 3,3'4,4'tetraalkyl meso phenyl dipyrromethane (0.25 mmol) or 2,2'-bis carboxy 3,3'-dialkyl meso phenyl dipyrromethane (0.25 mmol) are dissolved in N,N-dimethylformamide (10 ml) and the solution is heated to reflux under a stream of $N_2$, the reaction is monitored by TLC and when decarboxylation is complete the mixture is diluted with acetonitrile (10 ml) and cooled to −78° C. A solution of chlorosulfonyl isocyanate (2.9 mmol) in acetonitrile (1 ml) is added dropwise to the stirred solution under an atmosphere of $N_2$. The mixture is stirred for 1 hour at −78° C. and then for a further hour at −40° C. before being allowed to rise to room temperature. The reaction mixture is poured into a mixture of 5% aqueous sodium hydrogen carbonate (20 ml), aqueous potassium hydroxide (4 ml) and ice, then diluted with brine (200 ml) and extracted with dichloromethane (3×50 ml). The organic phase is washed with brine (5×100 ml), dried over anhydrous potassium carbonate, and the solvent is evaporated in vacuo. Chromatography of the residue gives 2,2'-bis cyano meso phenyl-3,3'4,4'-tetraalkyl dipyrromethane or 2,2'-bis cyano meso phenyltetraalkyl 3,3'-dialkyl dipyrromethane.

The bis cyano compound (0.11 mmol) is dissolved in dry THF (10 ml) and this solution is added dropwise to a stirred suspension of $LiAlH_4$ (1.3 mmol) in dry THF (10 ml) under an atmosphere of $N_2$ at 0° C. The reduction is monitored by TLC and when complete the excess $LiAlH_4$ is quenched with water, dichloromethane (15 ml) is added and the resulting slurry is gravity filtered. The filtrate is dried over anhydrous sodium sulfate and solvent is evaporated in vacuo. The residue is redissolved in dichloromethane (100 ml) and to the stirred solution is added dropwise a solution of DDQ (5 equivalents) in toluene (5 ml). The oxidation is followed by UV-vis spectroscopy and, when no further porphocyanine formation is observed, the reaction mixture is filtered through a plug of alumina. The filtrate is evaporated in vacuo and the residue is chromatographed to give 1,11-diphenyl β-octaethyl porphocyanine or 1,11-diphenyl β-tetraalkyl porphocyanine.

Example 11

Application of the Method of Example 10

Using the method of Example 10, the following was prepared:

12,24-Diphenyl-3,9,15,21-tetramethyl-2,10,14,22-tetramethyl porphocyanine: 100 mg 2,2'-bis carboxy 3,3'-diethyl-4,4'-dimethyl meso phenyl dipyrromethane gives 40 mg (44%) bis cyano 3,3'-diethyl-4,4'-dimethyl meso phenyl dipyrromethane. 40 mg bis cyano 3,3'-diethyl-4,4'-dimethyl meso phenyl dipyrromethane gives 90 μg (0.23%) of the title compound after chromatography (60–325 mesh neutral alumina; 10% ethyl acetate in dichloromethane).

Spectroscopic data: UV-vis: 462,604,642,802 nm in $CH_2Cl_2$; HRMS (EI) for $C_{46}H_{48}N_6$ ($M^+$) calcd. 684.3940, found 684.3932.

Example 12

In Vitro Toxicity of Porphocyanine

Cells are washed three times in serum-free medium (DME), counted and made up to a concentration of $10^7$ cells per ml.

For the "affinity" assay, in the dark, 100 μl of the cell suspension and 100 μl of the test or control compound are mixed. "Labeling" is allowed to continue for one hour at 4° C., and labeled cells are washed in the dark three times with 3 ml medium each time and resuspended in fresh medium. The resuspended cells are then subjected to light exposure at 300–850 nm for 30 minutes.

In a "direct" assay the cells are irradiated immediately upon addition of the test or control compound. The effect of irradiation is estimated using methods appropriate to the target cells.

When human erythrocytes (RBCs) are used as test cells, the hemolysis caused by irradiation of control (hematoporphyrin, Hp)-labeled and porphocyanine (formula (1))-labeled cells is estimated visually.

When the murine mastocytoma cell line P815 is used, the results are determined as follows:

The cells are labeled as above using concentrations of 10–50 ng/ml of Hp as control and the porphocyanine of formula (1a) as the test substance. The resuspended cells are treated with 300–850 nm light for 30 minutes and the viability resulting is estimated by direct counting using eosin-Y exclusion, a standard procedure for differentiating living from dead cells.

In other determinations conducted as above, the cells recovered from light exposure are assayed for viability by incubating them for 18 hours in 10 μCi/ml tritium-labeled thymidine according to the standard procedure whereby thymidine incorporation is equated with viability. The cells are harvested and radioactivity uptake is measured by a scintillation counter.

Example 13

Selective Binding of Porphocyanine

P815 cells are incubated as described in Example 12 using 1–200 ng/ml Hp or the porphocyanine of formula (1a). The cells are labeled in the dark for 30 minutes, washed free of unabsorbed porphyrins, resuspended, and then exposed to 300–850 nm light for another 30 minutes. Viability of the cells is established by tritiated thymidine incorporation after labeling with 30 μCi/ml tritiated thymidine and incubating at 37° C. for 18 hours.

Example 14

Preparation of Immunoconjugates

This example describes methods of preparation for immunoconjugates of four different antibody preparations with either hematoporphyrin (Hp) or a porphocyanine (Pc) of formula (1a). The antibodies employed are CAMAL-1, anti-M1 antibody, and B16G antibody, all prepared as described hereinabove, and affinity purified rabbit anti-mouse Ig (RαMIg). In addition, a purified irrelevant monoclonal preparation (C-MAb) is used where a control is desired.

One preparation of the conjugates is performed basically as described by Mew et al. *J Immunol* (1983) 130:1473). Briefly, to 220 mg Hp.0.2 HCl (Sigma Chemical Co., St. Louis, Mo.) in 25 ml water and 0.8 ml N,N-dimethylformamide is added 20 mg 1-ethyl-3-(3-dimethylaminopropyl)-carbodiimide HCl (EDCI) in 0.6 ml water. After 30 minutes, this solution is mixed with 15 mg of the antibody protein dissolved in 5 ml distilled water and incubated for 5 hours. During this period, the pH of the solution is monitored and adjusted to between 6 and 7. Then 50 μl of monoethanolamine is added, and the solution is allowed to stand overnight at room temperature. The solution is dialyzed against 0.001M phosphate buffer pH 7.4 for four days with three changes per day and overnight against PBS. The conjugate of porphocyanine is analogously prepared.

In a preferred protocol, 2 ml of a dispersion in DMSO containing 5 mg each of the Hp or Pc and the dehydrating agent is prepared and stirred for 30 minutes at room temperature under nitrogen. To this is added a dispersion containing 2 mg of the appropriate immunoglobulin in 2 ml of DMSO, and the resulting mixture stirred for another 10 minutes. This mixture is then worked up by dilution in phosphate-buffered saline, pH 7.4 (PBS) by adding 5 times the volume of PBS containing 50 µl monoethanolamine, and is then dialyzed against PBS using three changed of wash.

Alternatively, 2 ml of a dispersion containing 5 mg each of Hp or Pc, a linking agent, and a dehydrating agent is prepared and stirred for approximately 15 minutes at room temperature under nitrogen. To this is then added a dispersion containing about 2 mg of the immunospecific protein in 2 ml of tetrahydrofuran and the resulting mixture stirred for another 10 minutes. The mixture is then worked up as described above.

The foregoing procedures are appropriate for CAMAL-1 and for the remaining antibody preparations listed above.

In addition, the following preparations are made specifically with B16G and RαMIg:

B16G

Eleven mg of hematoporphyrin plus 11 mg of EDCI in 4 ml spectral grade DMSO are stirred for 30 minutes under nitrogen at room temperature before the addition of 20 mg lyophilized B16G antibodies, prepared as described by Maier et al. *J immunol* (1983) 131:1843, in 2 ml DMSO. The resulting mixture is stirred for 40 second at room temperature and working up as described above. The resulting product contains approximately 375 µg Hp/mg B16G. A similar procedure is used substituting Pc for RαMIg Four hundred µg of EDCI and 400 µg hematoporphyrin in 1 ml DMSO are stirred for 30 minutes under nitrogen at room temperature as above before the addition of 800 µg lyophilized RαMIg antibodies, prepared as described by Mew et al. *J Immunol* (1983) 130:1473) in 1 ml DMSO. The resulting mixture is stirred for 30 seconds and worked up as described above to obtain a product containing 200 αg Hp/mg RαMIg. A similar procedure is used substituting Pc for Hp.

Example 15

Specificity of Immunoconjugates In Vitro

The TSM-Hp and TSM-Pc conjugates wherein the TSM is comprised of an immunoglobulin are tested against cells in vitro by mixing the conjugates with the appropriate cell types, along with suitable controls, and then exposing the labeled cells to irradiation. Procedures for carrying out this assay are described in detail in Mew et al., Cancer Research (1985) for CAMAL-1, and by Mew et al., *J. Immunol.* (1983) for Anti-M1, both references cited hereinabove are incorporated herein by reference.

Briefly, for CAMAL-1, three cell lines, WC4, WC6 and WC2 (WC4 and WC6 produce the CAMAL antigen, but WC2 does not), are labeled with the appropriate TSM-Hp or TSM-Pc preparation as described above in Example 14. The labeled cell preparations containing $10^6$ cells each are introduced to Rose chambers and exposed to light activation with a laser at 630 nm. The results for various preparations are then compiled.

For the anti-M1 conjugate, M1 tumor cells are used as target cells and treated with the TSM-Hp, TSM-Pc conjugates or drug or antibody alone or the combination of antibody and drug, but uncoupled, by incubating them in 6% $CO_2$ humidified incubator at 37° C. for two hours. The cells are washed three times in PBS and then plated and exposed to fluorescent light overnight. The cells are assessed for viability by tritiated thymidine uptake as above.

For the B16G conjugates, A10, P815, and L1210 cells are used as target cells. (A10 cells are a T cell hybridoma which secretes a B16G-reactive T-suppressor factor; P815 cells are also reactive with B16G.) The in vitro study is done using a direct method employing the B16G-Hp or B16G-Pc conjugate or indirectly using unlabeled B16G antibodies and labeled RαMIg-Hp or RαMIg-Pc.

In a direct method, $5 \times 10^5$ cells are suspended in 1 ml DME/Hepes containing the appropriate TSM-drug conjugate as test or control at Hp or Pc concentrations of 320, 160, 80, 40 and 20 ng drug/ml. The cells are incubated in the dark at 37° C. for 1 hour, then washed 3 times in 5 ml DME/Hepes, and then resuspended in 1 ml of the same buffer. Three 100 µl test portions of the labeled preparations are dispensed into flat bottom microtiter wells and the remainder of the cell suspensions (700 µl) are exposed to incandescent light (22.5 mW/cm$^2$) at a distance of 20 cm for 1 hour. Then three additional 100 µl aliquots are removed to microtiter wells. Tritium-labeled thymidine diluted in DME/Hepes containing 20% FCS is then added to all microtiter wells in 100 µl aliquots so that 2 µCi of labeled thymidine is added to each well. Cultures are incubated for 18 hours at 37° C. and humidified 10% $CO_2$ and then harvested on a MASH harvester. Thymidine incorporation is measured with an Hp scintillation counter (Tri-Carb Model 4550). In an indirect assay, the A10 suspended cells, prepared as described above, are exposed to 50 µg/ml of either B16G or a control antibody C-MAb at 4° C. for 30 minutes, washed in DME/Hepes, and then exposed for an additional 30 minutes at 4° C. in the dark to varying concentrations of RαMIg-Hp or RαMIg-Pc between 2 µg/ml and 15 ng/ml of Hp or Pc. The cells are assessed for viability using labeled thymidine uptake as described above.

Example 16

In Vivo Cytotoxicity of the Porphocyanine and Conjugates Thereof

The in vivo efficacy of porphocyanine (Pc) and conjugates thereof is also assessed. For the CAMAL-1 and anti-M1 conjugates, the procedures are as described in the two Mew et al. papers referenced above in Example 15. For the B16G-Hp and B16G-Pc conjugates and for the Pc (formula (1)) alone, the in vivo studies are conducted as follows:

The in vivo test relies on the indirect effect of a population of T-suppressor cells on tumors, which then serve as means to assess the effectiveness of the irradiation treatment. P815 mastocytoma cells grown in syngeneic DBA/2 mice stimulate T-suppressor cells specific for the tumor. These T-suppressor cells impede the development of specific T-killer cells which would otherwise aid in the regression of the tumor. The T cell hybridoma designated A10 above secretes a T-suppressor factor which is associated with these T-suppressor cells. Thus, selective killing of these T-suppressor cell populations through reaction with conjugates in which the TSM is an antibody specific for the T-suppressor factor on the surface of the cells (namely B16G) should result in tumor regression in mice bearing the P815 tumors.

Therefore, in this assay, DBA/2 mice are injected in the right flank subcutaneously with $10^4$ P815 cells to incorporate the tumor. On day eight, when the tumors are palpable (approx. 25–42 sq. mm), the mice are randomly sorted into groups of eight and injected IV with 150 μl PBS containing nothing, Hp or Pc, B16G-Hp or B15G-Pc, B16G plus either drug, B16G alone or C-MAb-Hp or C-MAb-Pc. The levels of Hp are 50 μg per animal in all cases and B16G 310 μg in all cases (where appropriate).

The animals are maintained in the dark for two hours and then exposed to strong light at 300–850 nm and 22.5 mW/cm². The animals are then treated normally and monitored on a daily basis.

Example 17

Diagnostic Imaging

A 32-year old female patient develops fever and abdominal pain. The patient is maintained on antibiotic therapy for a period of one week without effect. A CAT scan fails to demonstrate any abnormal mass. Radioimaging studies are performed using Tc-99 m-labeled porphocyanine. An injection of 20 mCi of the radiolabeled porphocyanine is used and the patient is scanned with a gamma camera in SPECT mode. The scan of the patient's abdomen demonstrates a focus of accumulation of Tc-99 m. Surgery is performed and an abscess is found at the site of the Tc-99 m activity.

We claim:

1. A compound of the formula:

  (1)

and the metalated forms and salts thereof; wherein n is an integer of 1–4; and wherein each $P_i$ is independently a pyrrole residue of the formula

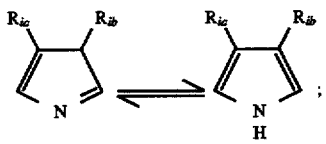

wherein each $Z_i$ is independently a covalent bond; or is a meso bridging group of the formula

an N-meso bridging group of the formula

; or is a CC linkage of the formula

or is a CNCCNC linkage of the formula

and wherein each $R_{ia}$, $R_{ib}$, $R_{ic}$, $R_{id}$, $R_{ie}$, $R_{if}$ and $R_{ig}$ is independently selected from the group consisting of: H, halo, nitro, cyano, —NR'₂, —SR', —OR', —SOR', —SO₂R', —COOR', —CONR'₂, optionally substituted alkyl (1–6C), optionally substituted alkenyl (1–6C), optionally substituted alkynyl (1–6C), optionally substituted aryl (4–12C), or optionally substituted arylalkyl (5–18C), wherein R' is H or alkyl (1–6C), R"CO— where R" is alkyl (1-6C) where $R_{ia}$ or $R_{ib}$ is —SR', —OR'; and said optional substituent is selected from the group consisting of halo, nitro, cyano, —NR'₂, —SR', —OR', —SOR', —SO₂R', —COOR', —CONR'₂ and, when said optional substituent is aryl or arylalkyl, said optional substituent may also be alkyl (1–6C), alkenyl (1–6C) or alkynyl (1–6C); or, if $R_{ic}$, $R_{id}$, $R_{ie}$, $R_{if}$ and $R_{ig}$, may also be a CNC linkage of the formula

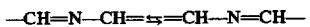

wherein at least one $Z_i$ is said CNC linkage.

2. The compound of claim 1 wherein n=2.

3. The compound of claim 2 wherein $Z_1$ and $Z_3$ are CNC linkages and $Z_2$ and $Z_4$ are meso linkages.

4. The compound of claim 2 wherein $Z_1$ is a CNC linkage and $Z_2$, $Z_3$ and $Z_4$ are meso linkages.

5. The compound of claim 2 wherein $Z_1$ is a CNC linkage, $Z_2$ and $Z_4$ are covalent bonds, and $Z_3$ is a CC linkage.

6. The compound of claim 2 wherein $Z_1$ and $Z_3$ are CNC linkages, $Z_2$ is a covalent bond and $Z_4$ is a meso linkage.

7. The compound of claim 2 wherein $Z_1$ and $Z_3$ are CNC linkages, $Z_2$ is a meso linkage, and $Z_4$ is a CNCCNC linkage.

8. The compound of claim 2 wherein $Z_1$ and $Z_3$ are CNC linkages, $Z_2$ is an N-meso linkage, and $Z_4$ is a meso linkage.

9. The compound of claim 2 wherein all of $Z_1$, $Z_2$, $Z_3$ and $Z_4$ are CNC linkages.

10. The compound of claim 1 wherein n=1.

11. The compound of claim 10 wherein $Z_1$ is a CNC linkage, and $Z_2$ and $Z_3$ are meso linkages.

12. The compound of claim 1 wherein n=3.

13. The compound of claim 12 wherein $Z_1$ and $Z_2$ are CNC linkages, and $Z_3$, $Z_4$ and $Z_5$ are meso linkages.

14. The compound of claim 1 wherein n=4.

15. The compound of claim 14 wherein $Z_1$ and $Z_4$ are CNC linkages and $Z_2$, $Z_3$, $Z_5$ and $Z_6$ are meso linkages.

16. The compound of claim 1 wherein each $R_{ic}$ is independently optionally substituted aryl, optionally substituted alkyl, optionally substituted arylalkyl or is H.

17. The compound of claim 16 wherein each $R_{ic}$ is independently optionally substituted aryl or H.

18. The compound of claim 3 wherein one $R_{ic}$ is substituted aryl and the other $R_{ic}$ is H.

19. The compound of claim 1 wherein all $R_{ia}$ and all $R_{ib}$ are identical.

20. The compound of claim 3 wherein $R_{1a}$, $R_{1b}$, $R_{4a}$ and $R_{4b}$ are identical to each other and wherein $R_{2a}$, $R_{2b}$, $R_{3a}$ and $R_{3b}$ are identical to each other but different from $R_{1a}$, $R_{1b}$, $R_{4a}$ and $R_{4b}$.

21. The compound of claim 20 wherein each of $R_{ia}$ and $R_{ib}$ is independently H or optionally substituted alkyl.

22. The compound of claim 2 which is selected from the group consisting of porphocyanine; 2,3,9,10,14,15,21,22-octaethylporphocyanine, 12,24-diphenylporphocyanine; 12,24-di(3',4',5'-trimethoxyphenyl)porphocyanine; 12,24-di (pentafluorophenyl)porphocyanine; 12-phenyl-2,3,21,22-tetraethyl porphocyanine, 12,24-diphenyl 2,3,9,10,14,15,21, 22-octaethyl porphocyanine and 12,24-diphenyl 3,9,15,21-tetraethyl-2,10,14,22-tetramethyl porphocyanine.

23. A pharmaceutical composition which is cytotoxic to specific cells or tissues when irradiated with light, which comprises an effective amount of the compound of claim 1 in admixture with at least one pharmaceutically acceptable excipient.

24. A pharmaceutical composition which is cytotoxic to specific cells or tissue when irradiated with light, which comprises an effective amount of the composition of claim 2 in admixture with at least one pharmaceutically acceptable excipient.

25. The compound of claim 1 which is in metalated form.

26. The compound of claim 19 wherein the metal is a paramagnetic ion.

27. The compound of claim 26 wherein the paramagnetic ion element is gadolinium(III) or manganese(II).

28. A magnetic resonance imaging (MRI) contrast agent comprising the compound of claim 1 in metalated form with a paramagnetic ion.

29. The compound of claim 1 which includes a radioisotope selected from the group consisting of technetium, indium and gallium.

* * * * *